United States Patent
Von Oepen et al.

(10) Patent No.: US 7,837,726 B2
(45) Date of Patent: Nov. 23, 2010

(54) VISIBLE ENDOPROSTHESIS

(75) Inventors: Randolf Von Oepen, Los Altos Hills, CA (US); Anton G. Clifford, Mountain View, CA (US); Travis R. Yribarren, San Mateo, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/375,381

(22) Filed: Mar. 13, 2006

(65) Prior Publication Data

US 2006/0235505 A1    Oct. 19, 2006

Related U.S. Application Data

(60) Provisional application No. 60/661,542, filed on Mar. 14, 2005.

(51) Int. Cl.
 *A61F 2/06*    (2006.01)
(52) U.S. Cl. .................... 623/1.44; 623/1.15; 623/1.34; 623/1.46
(58) Field of Classification Search ....... 623/1.13–1.21, 623/1.27, 1.32, 1.33, 1.34, 1.44, 1.46
See application file for complete search history.

(56) References Cited

U.S. PATENT DOCUMENTS

| | | | |
|---|---|---|---|
| 5,507,771 A | 4/1996 | Gianturco | |
| 5,843,175 A | 12/1998 | Frantzen | |
| 6,174,329 B1 * | 1/2001 | Callol et al. | 623/1.34 |
| 6,290,726 B1 * | 9/2001 | Pope et al. | 623/22.15 |
| 6,402,777 B1 | 6/2002 | Globerman et al. | |
| 6,565,599 B1 | 5/2003 | Hong et al. | |
| 6,638,301 B1 * | 10/2003 | Chandrasekaran et al. | 623/1.34 |
| 6,699,280 B2 | 3/2004 | Camrud et al. | |
| 6,723,119 B2 | 4/2004 | Pinchasik et al. | |
| 6,849,085 B2 * | 2/2005 | Marton | 623/1.13 |
| 6,923,829 B2 | 8/2005 | Boyle et al. | |
| 7,122,049 B2 | 10/2006 | Banas et al. | |
| 2002/0007209 A1 | 1/2002 | Scheerder et al. | |
| 2003/0105511 A1 | 6/2003 | Welsh et al. | |
| 2003/0144728 A1 | 7/2003 | Scheuermann | |

(Continued)

FOREIGN PATENT DOCUMENTS

EP    0 875 218    11/1998

(Continued)

OTHER PUBLICATIONS

U.S. Appl. No. 11/375,380, filed Mar. 13, 2006.

(Continued)

*Primary Examiner*—Corrine M McDermott
*Assistant Examiner*—Suba Ganesan
(74) *Attorney, Agent, or Firm*—Workman Nydegger

(57) ABSTRACT

A crack-resistant endoprosthesis for delivery in a body lumen can be comprised of a multilayered material. The multilayered material can include at least two layers having a boundary layer therebetween. The boundary layer is configured to inhibit cracks from propagating from a first layer to a second layer. The different layers can be comprised of the same materials or different materials. It can be preferred that the multilayered material have layers that are comprised of resiliently-flexible materials, shape memory materials, and/or radiopaque materials.

21 Claims, 6 Drawing Sheets

U.S. PATENT DOCUMENTS

| | | |
|---|---|---|
| 2004/0000046 A1* | 1/2004 | Stinson .................. 623/1.44 |
| 2004/0186551 A1 | 9/2004 | Kao et al. |
| 2004/0243217 A1 | 12/2004 | Andersen et al. |
| 2005/0222673 A1 | 10/2005 | Nicholas |
| 2006/0030932 A1 | 2/2006 | Kantor et al. |
| 2006/0173529 A1 | 8/2006 | Blank |
| 2006/0248698 A1 | 11/2006 | Hanson et al. |
| 2007/0213810 A1 | 9/2007 | Newhauser |
| 2007/0255094 A1 | 11/2007 | Von Oepen et al. |
| 2007/0276463 A1 | 11/2007 | Nissl et al. |
| 2008/0319528 A1 | 12/2008 | Yribarren et al. |
| 2010/0010622 A1 | 1/2010 | Lowe et al. |

FOREIGN PATENT DOCUMENTS

| | | |
|---|---|---|
| WO | WO 00/15151 | 3/2000 |
| WO | WO 02/24111 | 3/2002 |
| WO | WO 03/037221 | 5/2003 |
| WO | WO 03/075797 | 9/2003 |
| WO | WO 2004/043221 | 5/2004 |
| WO | WO 2006/099430 | 9/2006 |
| WO | WO 2006/099449 | 9/2006 |
| WO | WO 2006/099450 | 9/2006 |

OTHER PUBLICATIONS

U.S. Appl. No. 60/661,542, filed Mar. 14, 2005, Von Oepen et al.
U.S. Appl. No. 11/375,380, mailed Aug. 29, 2008, Office Action.
U.S. Appl. No. 11/374,923, mailed Oct. 16, 2008, Office Action.
U.S. Appl. No. 11/374,923, mailed Dec. 12, 2008, Office Action.
U.S. Appl. No. 11/375,380, mailed Dec. 8, 2008, Office Action.
U.S. Appl. No. 60/946,066, filed Jun. 25, 2007, Yribarren et al.
U.S. Appl. No. 12/548,268, filed Aug. 26, 2009, Lowe et al.
U.S. Appl. No. 11/374,923, filed Jun. 25, 2009, Office Action.
U.S. Appl. No. 11/958,311, filed Jun. 11, 2009, Office Action.
U.S. Appl. No. 11/958,311, filed Sep. 4, 2009, Office Action.

* cited by examiner

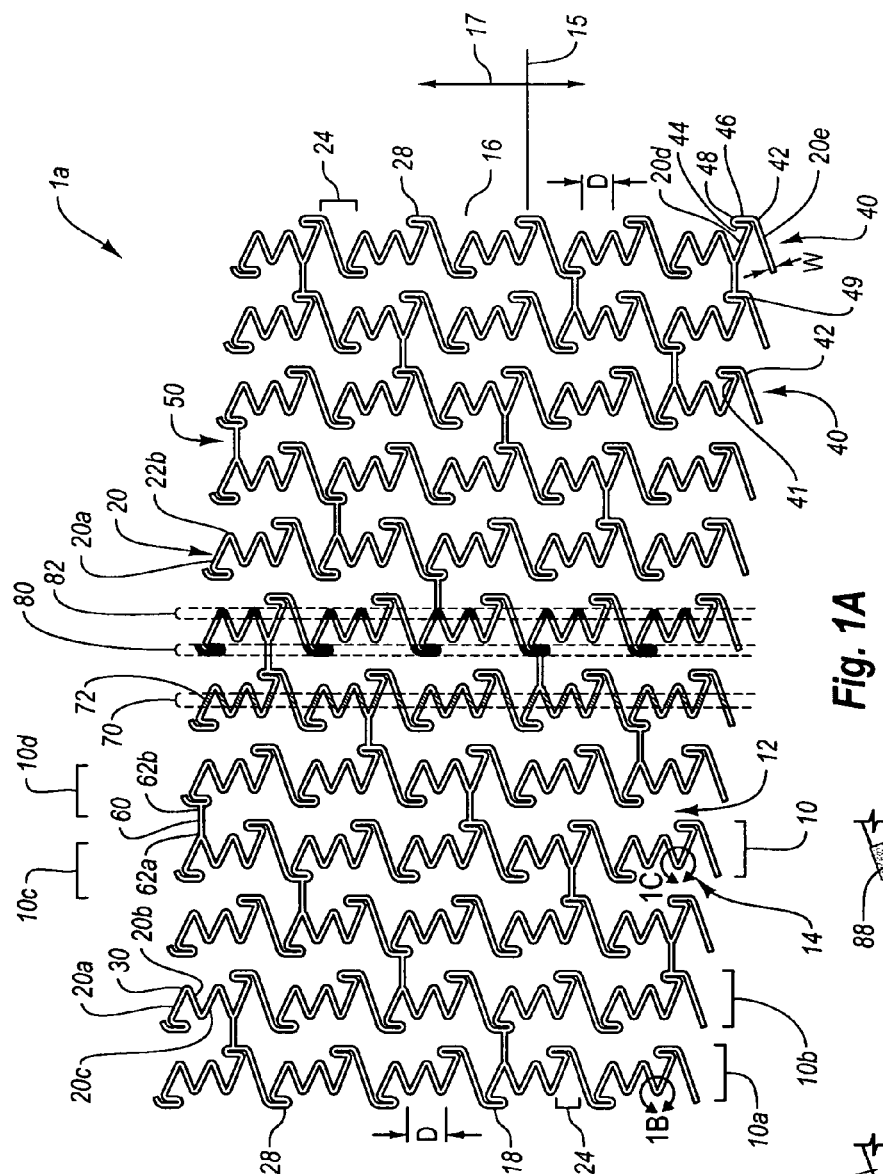

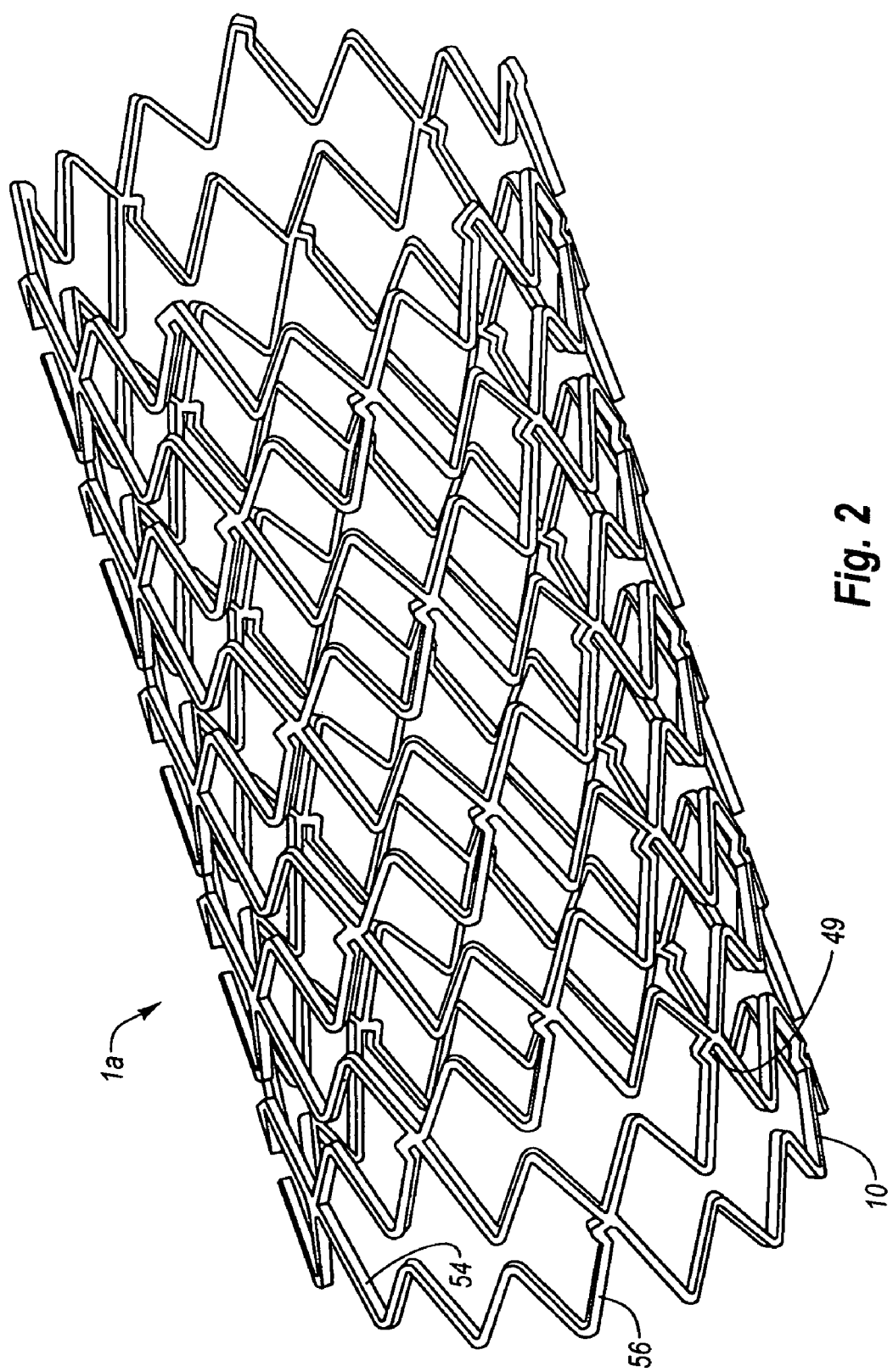

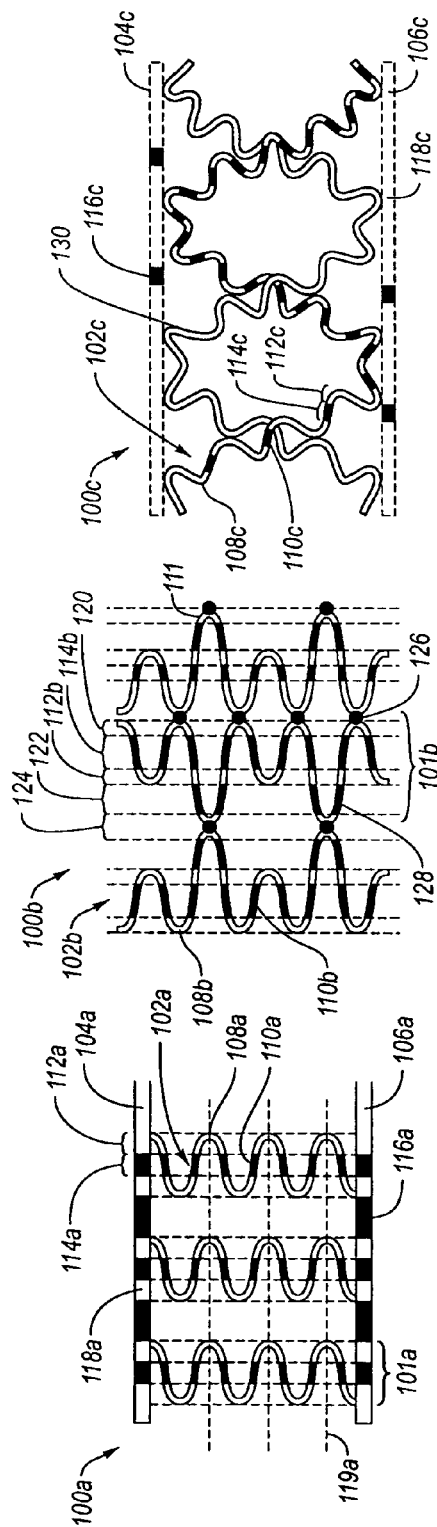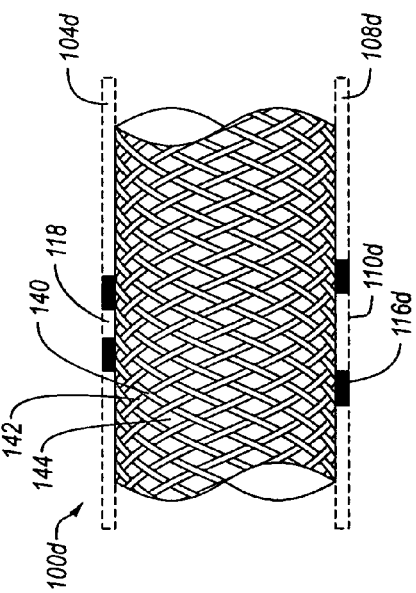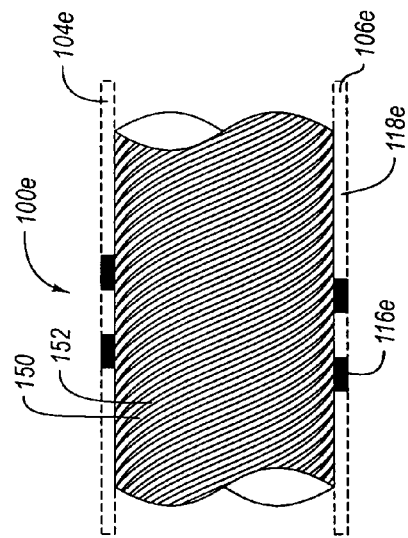

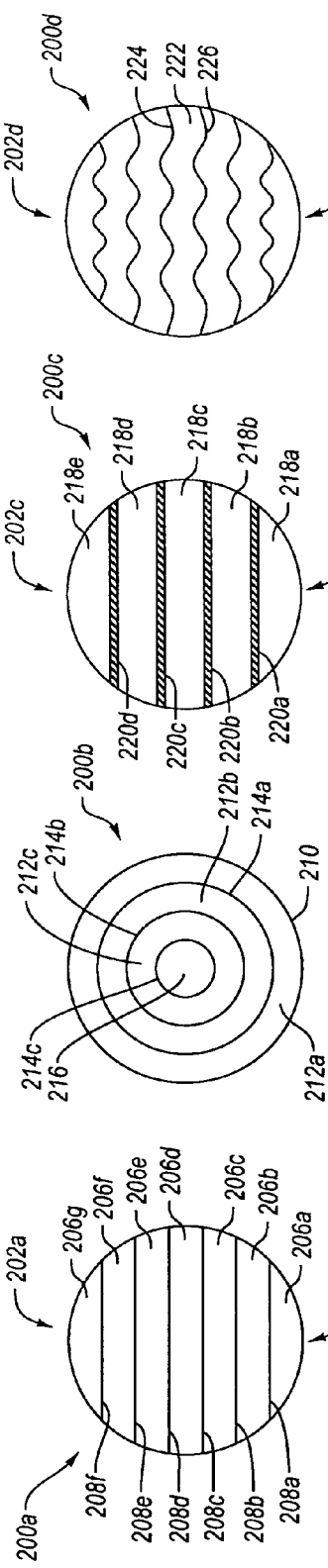
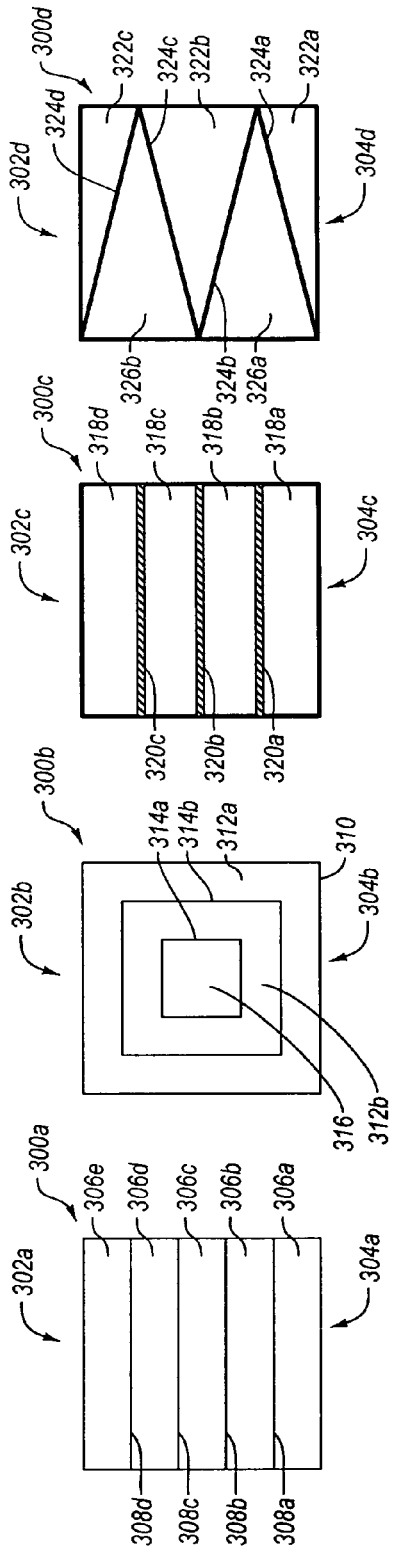

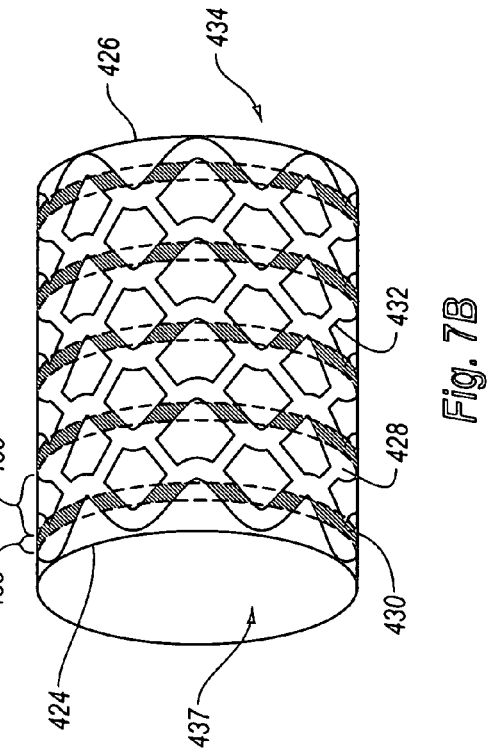
Fig. 7A
Fig. 7B
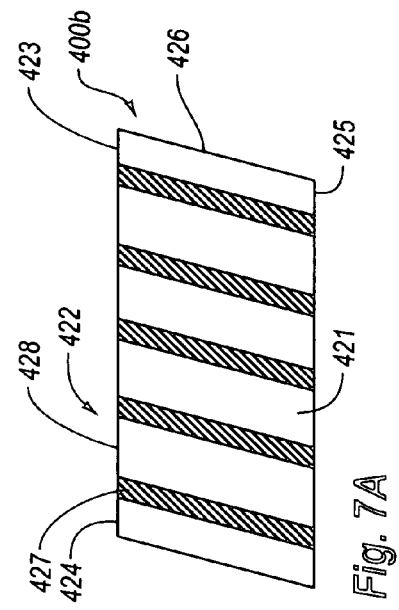
Fig. 6A
Fig. 6B
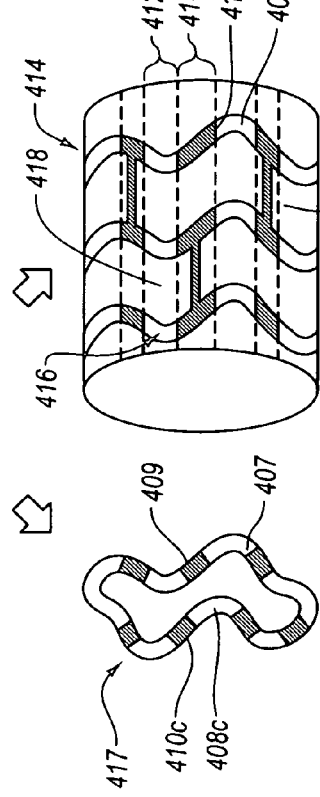
Fig. 6C
Fig. 6D

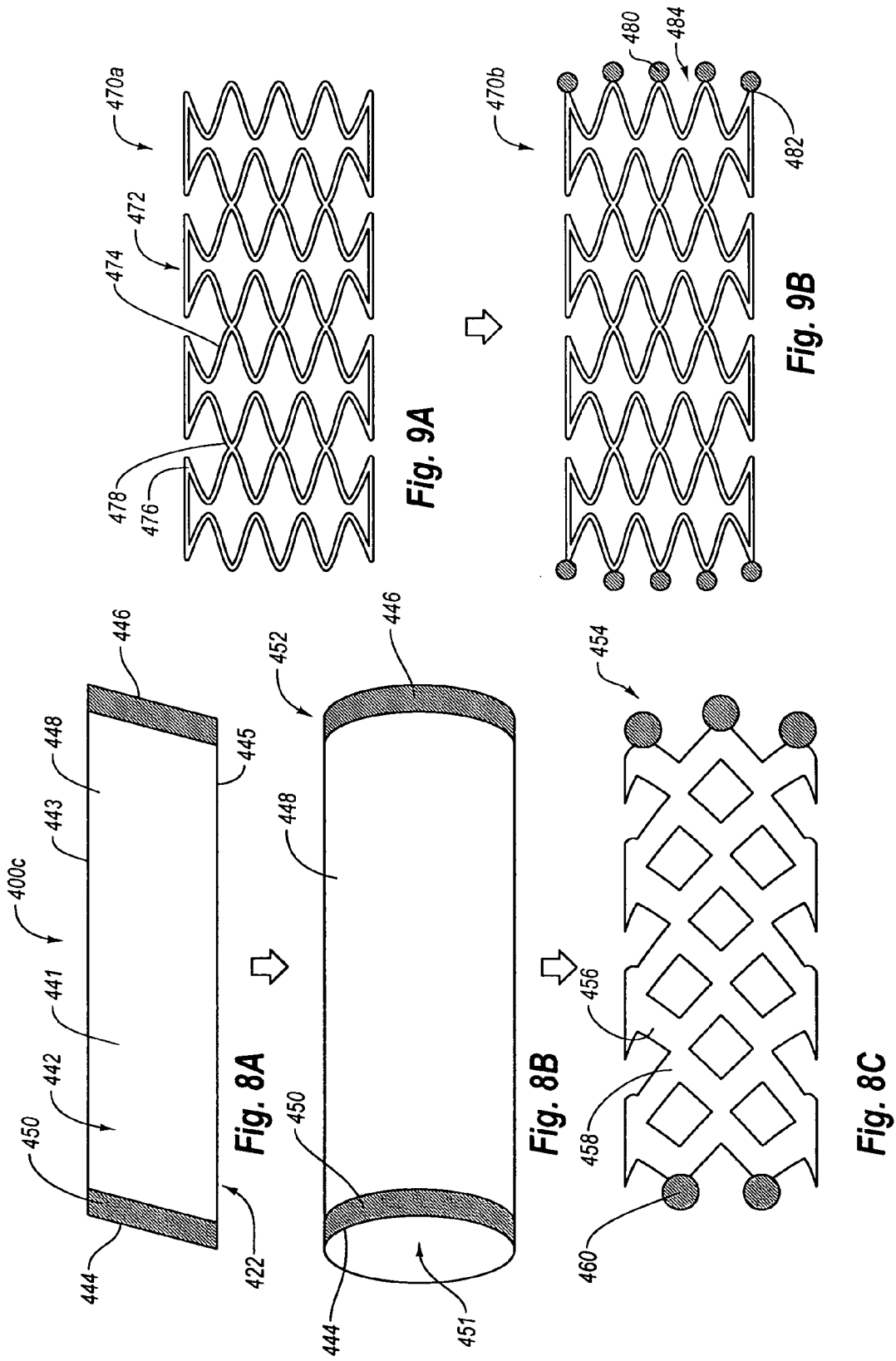

VISIBLE ENDOPROSTHESIS

CROSS-REFERENCE TO RELATED APPLICATIONS

This utility application claims benefit of U.S. Provisional Patent Application having Ser. No. 60/661,542 entitled "MULTI-LAYERD NITINOL TUBING FOR MEDICAL DEVICES," filed Mar. 14, 2005, which is incorporated herein by reference. This utility application also cross-references U.S. patent application Ser. No. 11/374,923, entitled "SEGMENTED ENDOPROSTHESIS" with Richard Newhauser as inventor, filed Mar. 13, 2006, and U.S. patent application Ser. No. 11/375,380, entitled "CRACK/FATIGUE RESISTANT ENDOPROSTHESIS" with Randolf Von Oepen as inventor, filed Mar. 13, 2006, wherein each is incorporated herein by reference.

BACKGROUND OF THE INVENTION

1. The Field of the Invention

The present invention relates to an endoprosthesis deliverable and deployable within a body vessel of a human or animal. More particularly, the invention relates to an endoprosthesis with improved visibility and/or crack and/or fatigue resistance capabilities.

2. The Relevant Technology

Stents, grafts, and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal, and can be deployed by any of a variety of recognized means. One recognized indication of endoprostheses, such as stents, is for the treatment of atherosclerotic stenosis, vulnerable plaque, dissections in blood vessels. For example, after a patient undergoes a percutaneous transluminal coronary angioplasty or similar interventional procedure a stent is often deployed at the treatment site to improve the results of the medical procedure and reduce the likelihood of restenosis. The stent is configured to scaffold or support the treated blood vessel; if desired, it can also be loaded with a beneficial agent so as to act as a delivery platform to reduce restenosis or the like.

An endoprosthesis is typically delivered by a catheter delivery system to a desired location or deployment site inside a body lumen of a vessel or other tubular organ. To facilitate such delivery, the endoprosthesis is typically capable of having a particularly small cross profile to access small diameter deployment sites. Additionally, the intended deployment site may be difficult to access by a physician and often involves traversing the delivery system through a tortuous luminal pathway. Thus, it can be desirable to provide the endoprosthesis with a sufficient degree of flexibility during delivery to allow advancement through the anatomy to the deployment site. Moreover, it may be desirable for the endoprosthesis to retain structural integrity during and/or after deployment and set.

Generally, an endoprosthesis can be constructed of multiple annular members or rings which are interconnected either through a connection section or a connection element. It is desirable for an endoprosthesis to have flexibility/stiffness properties to enable deployment through a tortuous luminal pathway yet have the stiffness properties which can be changed after deployment within a vessel. However, it can also be important for the endoprosthesis to retain its structural integrity after deployment by being configured to inhibit the formation and/or propagation of cracks as well as resist structural fatigue. Typically, flexibility can be controlled by the number and/or width of the rings and/or struts, the characteristics of the connection sections or elements, and/or the thickness of the material that forms the rings, the overall design of the endoprosthesis, material selection, length of the ring and or strut.

One problem with existing endoprosthesis designs relates to the difficulty in properly placing the endoprosthesis within a vessel prior to deployment of the endoprosthesis. Current endoprosthesis designs have thin struts which utilize less radiopaque material and therefore may not be as visible under fluoroscopy. An attempt to address the reduced radiopacity is to include radiopaque marker bands on the endoprosthesis, form the endoprosthesis of a radiopaque material or include marker bands on the delivery device. These marker bands may be located on the endoprosthesis to indicate an end of the endoprosthesis device, a length, a width, or the like. These marker bands have historically been soldered, welded, glued or press fit into hole features of the endoprosthesis device. A shortcoming of present designs is that the endoprosthesis are very difficult to manufacture, resulting in increased costs and manufacture time. Also, due to size limitations of the radiopaque material used, the markers may not provide sufficient visibility for precise placement.

Once deployed, the endoprosthesis can be capable of satisfying a variety of performance characteristics, as mentioned above. The endoprosthesis can be sufficiently rigid or provide an outwardly-oriented bias when deployed to perform its intended function, such as opening a lumen or supporting a vessel wall. Similarly, the endoprosthesis can have suitable flexibility along its length and/or width to inhibit any kinking or straightening that may occur during deployment or setting within a tortuous luminal pathway.

A significant failure mode in endoprostheses can occur as a result of crack formation and/or propagation through the body of an endoprosthesis. For example, failure can result from a stent element, such as a strut or elbow, beginning to crack during deployment, and subsequent propagation of the crack during setting and use. Such cracks can also initiate and/or propagate through the material of the endoprosthesis as a result of the cyclic loading that the stent undergoes during the pulsatile movement of blood and associated vessel expansion and contraction. For example, endoprosthetic fatigue failures can be encountered when nitinol stents are used in the superficial femoral artery ("SFA").

Although various endoprostheses have been developed to address one or more of the aforementioned performance characteristics, there remains a need for a more versatile design that improves one or more performance characteristics without sacrificing the remaining characteristics.

SUMMARY OF THE INVENTION

Therefore, it would be advantageous to have an endoprosthesis configured to have increased radiopacity to improve its visibility before, during, and after deployment. Additionally, it would be beneficial to have an endoprosthesis with improved resistance to cracking and/or fatiguing during deployment, setting, or use. Also, it would be beneficial for the endoprosthesis to have sufficient strength, flexibility, and radiopacity to enable enhanced deployment through tortuous luminal pathways while retaining the ability to perform its intended function.

Generally, the present invention includes endoprostheses for delivery into a lumen of a body. The endoprostheses can be configured to provide the desired deliverability, strength, flexibility, and/or functionality during and after deployment. For instance, the endoprostheses can be configured to have resistance to cracking and retain substantial structural integrity. Further, the endoprostheses can include radiopaque features that increase its visibility during use.

In one configuration, increased visibility and resistance to cracking can be achieved through tailoring combinations and orientations of multiple layers of material. The use of multiple layers within an endoprosthesis can also improve crack- and/or fatigue-resistance so as to retain substantial structural integrity after deployment. The inhibition of cracking can prevent portions of the endoprosthesis from puncturing the lumen or damaging the tissue of the lumen as well as retain luminal support of the treated lumen. In part, this is because a crack that propagates through a first layer of material will reach a junction between two adjacent layers and terminate. The boundary between the adjacent layers, whether or not such boundary is a separate boundary layer, can act to inhibit crack propagation because the crack will be less likely to continue through a different layer.

To provide the increased or enhanced visibility, one or more layers of the multiple layer structure can be formed from radiopaque material. By combining the radiopaque material with at least one layer of shape memory material, desired flexibility, crack resistance, and visibility characteristics can be achieved.

In another configuration, an endoprosthesis can include selectively placed radiopaque material and/or shape memory material. For instance, a first strut element can have a low stress zone of a radiopaque composite material having a plurality of adjacent layers that includes at least one radiopaque layer. A first boundary region, such as a boundary layer, can delineate adjacent layers and inhibit a crack from propagating between adjacent layers. A second-strut element can include a high stress zone adjacent to the first strut element. The high stress zone can have a resiliently-flexible composite material, such as a shape memory material, having a plurality of layers that includes at least one resiliently-flexible layer. A second boundary region, such as a boundary layer, can delineate adjacent layers and inhibit a crack from propagating between adjacent layers. Optionally, the radiopaque composite and resiliently flexible composite can each include a continuous layer that extends along the first strut element and the second strut element.

In another configuration, an endoprosthesis can have a plurality of braid elements braided together so as to form a braided tube. The braid elements can have a first set and second set of braid elements. The first set of braid elements can have a substantially first orientation, such as clockwise, and the second set of braid elements can have a substantially second orientation, such as counterclockwise that intersects with the first direction. These braided elements can provide the desired visibility properties, while maintaining the desired flexibility capabilities. The braided elements orientated orthogonal to the stress will avoid cracking. Optionally, the braided tube can be bound to the first tubular member. Optionally, the first tubular member can include at least one of a radiopaque material, a ceramic, a polymer, or a shape memory alloy. The braided tube can also be concentric with the first tubular member. If desired, the braided tube can be drawn down to form a unitary member having a plurality of layers configured to resist the propagation of discontinuities through the tubular member.

These and other embodiments and features of the present invention will become more fully apparent from the following description, drawings, and/or appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIGS. 1A-C is are planar side views of portions of an embodiment of an exemplary endoprosthesis in accordance with the present invention;

FIG. 2 is a perspective view of an embodiment of an expanded tubular endoprosthesis in accordance with the present invention;

FIGS. 3A-3E are side views of portions of embodiments of exemplary endoprostheses in accordance with the present invention;

FIGS. 4A-4D are cross-sectional profiles of an embodiment of an exemplary multilayered endoprosthesis body in accordance with the present invention;

FIGS. 5A-5D are cross-sectional profiles of an embodiment of an exemplary multilayered endoprosthesis body in accordance with the present invention;

FIGS. 6A-6D are schematic representations of embodiments of different stages of endoprosthesis manufacturing in accordance with the present invention;

FIGS. 7A-7B are schematic representations of embodiments of different stages of endoprosthesis manufacturing in accordance with the present invention;

FIGS. 8A-8C are schematic representations of embodiments of different stages of endoprosthesis manufacturing in accordance with the present invention; and FIGS. 9A-9B are schematic representations of embodiments of different stages of endoprosthesis manufacturing in accordance with the present invention.

DETAILED DESCRIPTION OF THE PREFERRED EMBODIMENTS

The present invention includes various embodiments of endoprostheses for delivery into a lumen of a body. The endoprostheses can be configured to have improved functionality by, in one configuration, being composed of multiple layers of materials that inhibit crack propagation through adjacent layers. As used herein, the term "layer" can refer to a distinct layer with a distinct separation between adjacent layers. Optionally, the term "layer" can refer to a structurally significant layer that imparts mechanical property to the endoprosthesis and can range in thickness so as to contribute to the overall strength of the endoprosthesis. As such, layers are typically not coatings that do not provide structural integrity or strength to the endoprosthesis.

The use of multiple layers can combine multiple functionalities into a single endoprosthesis. The use of multiple layers can impart improved crack and/or fatigue resistance by including crack propagation-inhibiting junctions between adjacent layers. By so doing, catastrophic failure can be prevented and portions of the endoprostheses from puncturing the lumen or damaging the tissue of the lumen. The selection and placement of multiple layers can increase the ability of the endoprostheses to sustain cyclic loading without suffering fatigue-related failures. Thus, the endoprostheses having the multiple layers can retain substantial structural integrity after deployment.

In addition to the above, the materials forming the layers can be selected to increase the visibility of the endoprostheses. For example, one layer having a higher radiopacity than the surrounding layer can be included to improve visualization during deployment and one layer can be a superelastic material to increase setting after deployment. Generally, reference to a layer of radiopaque material refers to a layer that has a radiopacity higher than at least one other layer. The inclusion of this layer increases the radiopacity of the endoprosthesis.

Thus, inhibiting crack propagation and/or fatigue-induced catastrophic failure can improve the safety and longevity of endoprostheses. For example, when a crack begins at the edge of a strut, as it propagates, it will encounter a junction or boundary between two adjacent layers. The junction between the layers, whether it is the interface between adjacent layers or a separate boundary layer, can then prevent further propagation from the cracked layer to the adjacent, un-cracked layer. In addition, the plurality of adjacent layers may also create a stronger structure since the materials can act like a plurality of interconnected flexible bodies.

More specifically, each layer can be selected based on the placement of the layer with respect to the surface, and/or on the adjacent layer materials to achieve different properties and characteristics for the endoprosthesis, as will be discussed in more detail hereinafter, the outer layer and inner layer being that of a superelastic biocompatible material such as Nitinol. For instance, in one configuration, the endoprosthesis can be formed from concentrically placing multiple tubes of a shape memory material before the tubes are drawn together to form the desired composite tubular structure, such as a two-layer or multi-layer Nitinol composite tubular structure.

Different types and numbers of multiple layers can be used for different purposes. For instance, this can include endoprosthetic elements that undergo significant bending and are high stress zones (e.g., elbows) being comprised of multiple layers of superelastic materials. These high stress zones can be substantially devoid of layers of harder materials.

As used herein, the term "catastrophic failure" is meant to refer to a section of an endoprosthesis breaking into multiple portions. For example, catastrophic failure of an elbow can result in a separation of the elbow from the adjacent strut member. Also, it can result in portions of the endoprosthesis coupled by the elbow to become uncoupled, where the ends of the break can adversely interact or puncture adjacent luminal tissue and/or supporting tissue, or project into the vessel lumen thereby leading to the formation of thrombosis or blockage of fluid flow therethrough and failure of tissue support.

I. Endoprosthesis

In accordance with the present invention, an endoprosthesis can be provided for delivery within a body lumen of a human or other animal. The present invention will be described with respect to a stent. As used herein the term stent and endoprosthesis are interchangeable. It will be understood, however, that various other endoprosthesis' and/or other medical devices can benefit from the teaching contained herein. For instance, other endoprosthesis or medical devices can include, but are not limited to, filters, grafts, valves, occlusive devices, aneurysm treatment devices, or the like. Additionally, an endoprosthesis can be configured for a variety of intralumenal applications, including vascular, coronary, biliary, esophageal, urological, gastrointestinal, nasal, or the like.

Following hereinafter is a general description of an exemplary embodiment of a stent 1a in accordance with the present invention. Following the general description, a more detailed description is provided. Turning to FIGS. 1a-2, an endoprosthesis 1a, such as a stent, can include at least a first set of interconnected strut elements that cooperatively define an annular element. A strut element can be more generally described as an endoprosthetic element, wherein all well-known endoprosthetic elements can be referred to here as a strut element for simplicity. Usually, each strut element can be defined by a cross-sectional profile as having a width and a thickness, and including a first end and a second end bounding a length. The length can be substantially linear, arced, rounded, squared, other configurations and/or combinations thereof. The strut element can have improved structural integrity by including a plurality of layers across a given cross-sectional profile in an amount, distribution, thickness, material selection, and/or configuration that can inhibit crack propagation and/or fatigue-induced catastrophic failure. The strut element can include a crossbar, connector, elbow, foot, ankle, toe, heel, medial segment, lateral segment, combinations thereof, or the like, as described in more detail below.

In accordance with the present invention, an endoprosthesis having a specific pattern will be described. It shall be understood that the following description of the endoprosthesis should not be considered limiting in any manner and that the inventions in accordance with the present invention are independent of the endoprosthesis pattern. For example, it is contemplated that the present invention may be practiced in accordance with endoprosthesis patterns having: connection sections, connectors; open cell patterns, close cell patterns and the like.

In accordance with the present invention, the annular elements include a plurality of circumferentially-adjacent crossbars that are interconnected end-to-end by an elbow connection or a foot extension. As such, at least one annular element can include an elbow or a foot extension ("foot") extending between at least one pair of circumferentially-adjacent crossbars. The elbow or foot can thus define an apex between the pair of circumferentially-adjacent crossbars of the annular element. Any of the crossbars, elbows, and/or foot elements can include planar or concentric layers that inhibit crack propagation from one layer through an adjacent layer and/or increase the visibility of the crossbars, elbow, and/or foot elements.

The elbow can be configured in any shape that connects adjacent ends of circumferentially-adjacent crossbars, and can be described as having a U-shape, V-shape, L-shape, or the like. The foot can have a foot shape having a first foot portion extending circumferentially from an end of one of the adjacent strut members and a second foot portion extending circumferentially from a corresponding end of the other of the circumferentially-adjacent strut members. In combination, the first and second foot portions generally define an ankle portion connected to a toe portion through a medial segment and the toe portion connected to a heel portion through a lateral segment.

In one embodiment, an endoprosthesis can include two or more interconnected annular elements. As such, the endoprosthesis can include at least a second set of interconnected strut elements defining at least a second annular element. Also, the endoprosthesis can include additional annular elements defined by interconnected strut elements as described herein or well known in the art. Each annular element can generally define a ring-like structure extending circumferentially about a longitudinal or central axis. The cross-sectional profile of each annular element can be at least arcuate, circular, helical, or spiral, although alternative cross-sectional profiles, such as oval, oblong, rectilinear or the like, can be used.

In one embodiment, a first annular element can be aligned longitudinally adjacent to a second annular element along the longitudinal axis, and connected to each other at at least one connection element, wherein the connection element may be a connection section or a connector element extending between the two annular elements. The connector element can be considered as a strut element for the purposes of the invention, and can optionally have a plurality of holes therein. As such, the connector element can be a strut element that interconnects adjacent annular elements, and has improved structural integrity by having a plurality of layers to inhibit crack propagation in accordance with the present invention.

The first and second annular elements generally define a tubular structure. For example, each annular element can define a continuous closed ring such that the longitudinally-aligned annular elements form a closed tubular structure having a central longitudinal axis. Alternatively, each annular element can define an open ring shape such that a rolled sheet, open tubular, or "C-shape" type structure is defined by the annular elements. That is, the annular element is not required to be closed. Furthermore, each annular element can define substantially a 360 degree turn of a helical pattern or spiral, such that the end of one annular element can be joined with the corresponding end of a longitudinally-adjacent annular element to define a continuous helical pattern along the length of the endoprosthesis.

Each strut crossbar of the annular elements can include a first end and a second end. The crossbar of each annular element can be disposed circumferentially adjacent to each other, and interconnected through elbow elements, foot elements, and/or the like so as to define an expandable structure. For example, and with reference to the closed tubular structure described above, circumferentially-adjacent crossbars of each annular element can be interconnected, either directly or indirectly, in an end-to-end format by an elbow, foot, and/or the like to define a continuous ring having a generally circular cross-sectional profile. By altering the angle or distance defined between circumferentially-adjacent crossbars, the tubular structure can be radially expanded between a delivery configuration and a deployed configuration. As discussed in detail below, the expandable structure can be expanded by the application of an external force, such as by a balloon, or by a change in delivery conditions, such as an increase in temperature or the removal of a restraint, so as to allow the structure to self-expand.

In one embodiment, one or more of the strut elements of an annular element can include a plurality of planar or concentric layers of materials that prevent crack propagation. Additionally, other configurations of multilayered materials can be used in any of the strut elements. One or more of the strut elements can include cross-sectional profiles having a plurality of layers. A cross-sectional profile of any particular strut element can have at least two layers, but can have three or more layers that extend along all or a portion of the length of the strut body. This can be exemplified by a cross-section of the strut element being partitioned into two or more discrete layers that are separated by a junction or boundary therebetween.

While the present invention is described and illustrated with the cross-sectional profile of a width and thickness of a strut element having multiple layers that extend along the length, it should be recognized that the layers can be concentric or planes that extend between any points around the perimeter of a cross-sectional slice of the strut element. Also, the multiple layers can have any orientation or angle with respect to the length and/or cross-section of the strut element. Also, while one exemplary embodiment of an endoprosthesis is shown to include crossbars that are interconnected by elbows or foot extensions to form annular elements, which are in turn interconnected by connectors to form a tubular endoprosthesis, such embodiment is not limiting and merely provided as one type of endoprosthesis that can be prepared in accordance with the present invention.

With continued reference to FIG. 1A, illustrated is a side view of a flattened portion of an embodiment of an endoprosthesis 1a having a plurality of layers of material. For purposes of illustration and not limitation, a representative embodiment of the endoprosthesis 1a of the present invention in a deployed configuration is depicted in a planar format for clarity. As shown, the endoprosthesis 1a can include a plurality of annular elements 10 aligned longitudinally adjacent to each other along a longitudinal axis 15. Although only one annular element can be used, the endoprosthesis can include a plurality of annular elements 10, depicted herein for purposes of illustration by at least a first annular element 10a and a second annular element 10b.

Each annular element 10 can include a set of interconnected strut elements shown as strut crossbars 20, which are disposed circumferentially about the longitudinal axis 15. Arrows 17 illustrate the circumferential directionality. Each crossbar 20 can have a first end 22a and a second end 22b, referenced generally as end 22. The first end 22a of selected circumferentially-adjacent crossbars 20a-b can be interconnected at elbows 30 that are proximate to a first longitudinal side 12 of each annular element 10, and the second end 22b of selected circumferentially-adjacent crossbars 20b-c can be interconnected to define elbows 30 that are proximate to a second longitudinal side 14 of the annular element.

Each annular element 10 can be expanded to a deployed configuration as shown in FIG. 1A by altering or opening the angle of the elbows 30 interconnecting the circumferentially-adjacent crossbars 20, or can be collapsed into a deployable configuration by closing the angle of the elbows. Also, circumferentially-adjacent elbows 30 on each side 12, 14 of the annular element 10 can be spaced apart by a circumferential distance D, such that each annular element 10 is expanded by increasing the distance D and collapsed by decreasing the distance D. At any given condition between the delivery configuration and the deployed configuration, the distance D can be balanced or constant from one set of circumferentially-adjacent elbows to the next, or it can be varied if desired.

Selected elbows 30 on each side 12, 14 of the annular element 10 can be defined by interconnecting corresponding ends 22 of circumferentially-adjacent crossbars 20a-b directly together to form: a zigzag pattern of alternating U-shapes, V-shapes, L-shapes, combinations thereof, or the like when deployed. Alternatively, an elbow 30 can be provided between the corresponding ends of adjacent crossbars to form another contoured shape, such as by using a straight elbow member to form a flat connection configuration, or a curved elbow member to form an arcuate connection configuration.

FIG. 1A also depicts an embodiment of a foot extension 40 that can extend between a pair 24 of circumferentially-adjacent crossbars 20d-e of each annular element 10. As depicted, the foot extension 40 can include an ankle 41 that circumferentially couples an end 22 of one of the adjacent crossbars 20d to a medial segment 44. The medial segment 44 extends from the ankle 41 to a toe 48 that circumferentially couples the medial segment to a lateral segment 46. The lateral segment 46 extends from the toe 48 to a heel 42 that circumferentially couples the lateral segment to the next circumferentially-adjacent crossbar 20e. Accordingly, the juncture of the crossbar 20d and the medial segment 44 defines a circumferentially-extending toe portion 48 of the foot extension 40; the juncture of the medial segment 44 and the lateral segment 46 defines a circumferentially-extending toe portion 48 of the foot extension 40; and the juncture of the lateral segment 46 and crossbar 20e defines a circumferentially-extending toe portion 48 of the foot extension 40. Each portion of the foot extension 40, as well as each of the circumferentially-adjacent crossbars 20, can have a substantially uniform cross-sectional profile illustrated by a substantially uniform width W and thickness (not shown).

Additionally, for purpose of discussion and not limitation, FIG. 1A shows that a toe portion 48 can extend in a first circumferential direction a distance greater than the heel portion 42 of the foot extension 40 extends in an opposite circumferential direction. As such, the entirety of the foot extension 40 can extend in the circumferential direction of the toe portion 48. Furthermore, at least one of the medial segment 44 or lateral segment can open foot region 49 (see also, FIG. 2).

In one embodiment, areas more susceptible to high stress or strain can include multiple layers of material to aid in preventing crack propagation and/or increasing the visibility of the endoprosthesis 1a. Since the elbows 30 and/or foot extensions 40 connect circumferentially adjacent crossbars 20, the elbows and foot extensions can be susceptible to higher levels of stress or strain. Accordingly, the elbows 30 and foot extensions 40 can be favorable locations for including multiple layers of materials. This can be shown by a first strain area 80, which includes the different portions of foot extensions 40, including multiple layers of materials. Also, a second strain area 82, which includes the elbows 30, can include multiple layers of materials. Moreover, the multiple layers of materials can be located at the first strain area 80, second strain area 82, and/or any other high stress or strain area about the entire annular element 10.

In one embodiment, areas less susceptible to high stress or strain can include multiple layers of stiffer materials to aid in increasing the strength of the endoprosthesis. Since the elbows 30 and/or foot extensions 40 connect circumferentially adjacent crossbars 20, the crossbars 20 can be less susceptible to higher levels of stress or strain. Accordingly, the crossbars 20 can include multiple layers of less flexible materials or stronger materials compared to the materials or multiple layers of the elbows 30 and foot extensions 40. This can be shown by a less flexible zone 70 at a crossbar 20 having multiple layers of stronger or less flexible materials. Also, the less flexible zone 70 can include at least one layer of a radiopaque material 72. In part, this is because radiopaque materials may be stronger or less flexible than superelastic materials or other materials for use at elbows 30 and/or foot extensions 40. Thus, multiple layers of materials that include at least one layer of a radiopaque material 72 can be advantageously employed at areas of less deformations 70 of crossbars, as well as at connectors 60 or the like.

In this illustrated configuration, a plurality of connectors 60 can be provided to connect adjacent annular elements 10c-d at a plurality of connection locations 50. Each connection location 50 can include a portion of the adjacent annular element 10. As shown, by way of example, the connection location 50, a foot extension 40 of one annular element 10d, and an elbow 30 of the adjacent annular element 10c, with a connector 60 having opposite ends 62a-b connected therebetween. Alternatively, the connector 60 can extend from elbow-to-elbow, foot-to-foot, foot-to-elbow, crossbar-to-crossbar, more specifically, any location of one annular element to another spaced grant apart annular element, whether or not adjacent, and the like.

As shown, the adjacent annular elements 10c-10d can be coupled by an elbow connector end 62a being coupled to an elbow 30, and an opposite foot connector end 62b being coupled to a foot. More particularly, the foot connector end 62b of the connector can be coupled to the lateral segment 46 of the foot extension 40. With a connector 60 extending longitudinally from the lateral segment 46 of a foot extension 40 to an elbow 30, the longitudinally-adjacent elbows 30 of adjacent annular elements 10c-10d can be circumferentially out of alignment. The foot lateral segments 46 at the longitudinal ends 16, 18 of the endoprosthesis 1a can face outward from the remainder of the structure.

One or more foot extensions 40 at either end 16, 18 of the endoprosthesis 1a can include an area that undergoes minimal deformation or strain, such as the lateral segment 46, when expanded to the deployed configuration or collapses into a deployable configuration. It will be understood that other portions of the endoprosthesis 1a can undergo minimal deformation or strain, such as but not limited to, other strut elements, etc. Due to the minimal strain actuating open those elements or segments, these elements or segments can be optionally narrowed to have a cross-section smaller than the remainder of the endoprosthesis, as shown in FIG. 1B. This narrowed portion can then be wrapped with a wire or strip of radiopaque material 84 so as to act as a radiopaque marker 28 for imaging purposes.

Alternatively, with reference to FIG. 1C, one or more holes or grooves 86 can be formed in those segments or elements having laser etching, photo-etching, or other process suitable to create the holes or grooves. These holes or grooves 86 can be filled with a radiopaque material 88 using a process, such as, but not limited to, ink-jet printing, sputtering, electric-deposition, riveting, crimping, or other suitable processing materials or techniques. This increases the visibility of those portions and also the visibility of the endoprosthesis 1a. To aid with viewing the holes or groove 86 and the radiopaque material 88, this configuration of FIG. 1C illustrates unfilled holes and filled holes. It will be understood that in use the holes or grooves 86 would be filled. The identified areas of minimal deformation or strain can be particularly suited for multiple layers, which optionally include layers of radiopaque materials. The holes or grooves 86 may also serve as depots or reservoirs for a beneficial agent, wherein the beneficial agent may be configured to be released from the hole or groove as known in the art. Examples of suitable beneficial agents are described in U.S. Pat. No. 6,015,815 titled Tetrazol-Containing Rapamycin Analogs With Shortened Half-Lives, the entirety of which is hereby incorporated by reference.

For simplicity and clarity, each crossbar 20 and connector 60 depicted in FIG. 1A is shown to be a straight member. It is recognized, however, that the crossbars 20 and connectors 60 can be contoured or shaped to increase longitudinal flexibility if desired. Similarly, the crossbars and/or connectors need not extend parallel to the longitudinal axis, but can be aligned diagonally or helically such that the ends of the connector are circumferentially offset.

FIG. 2 shows an exemplary embodiment of an endoprosthesis 1a in a deployed and expanded orientation. In FIG. 2, the tubular endoprosthesis 1a illustrates the sides 54 and tops 56, both of which can include the plurality of layers. Also, it should be noted the endoprosthesis 1a can define an open ring to form a rolled sheet or open tubular type structure, can define adjacent turns of a continuous helical pattern, or other like shapes that can function as described herein.

Similarly, the radial bias, rigidity, flexibility, crack resistance, fatigue resistance, and other physical characteristics of each annular element 10 can be controlled or varied by altering the shape or size of the crossbars, elbows, feet, connectors, and the like. The physical characteristics of the annular element 10, when deployed, generally can be increased by decreasing the length or by modifying the cross-sectional profile of selected strut elements of the annular element 10. For example, it can be possible to provide an endoprosthesis having varied radial bias or rigidity along its length by providing one annular element with a radial bias or rigidity that is different from the radial bias or rigidity of another annular element as is well known in the art. In a similar manner, it is possible to provide an endoprosthesis having a tapered or flare shape formed of adjacent annular elements having different cross-sectional profiles when in the deployed configuration, but similar or uniform radial bias or rigidity along its length. It will be understood that the description of the various endoprostheses can apply to each other. As such, the discussions herein can apply to each other and to various other devices.

Turning to FIG. 3A, illustrated is a side view illustrating a flattened portion of another configuration of an endoprosthesis 100a. The endoprosthesis 100a is shown to include a plurality of strut elements 102a spaced apart by at least a first rail 104a and second rail 106a. This is in contrast to the configuration of FIG. 1, where adjacent annular elements were spaced apart by way of connectors 60.

With continued reference to FIG. 3A, the rails 104a, 106a can be radially disposed on the endoprosthesis 100a and any number of rails can be used. For instance, although only two rails 104a and 106 are depicted, an endoprosthesis can include one or more rails around a periphery of the annular elements and/or interlaced or weaved through the annular elements. The rails 104a, 106a can be used to connect separate strut elements or annular elements 101a in order to form a tubular endoprosthesis 100a. The rails 104a and 106a can be fabricated from a single material or a multi-layer material, as described in more detail below. Also, the rails 104a and 106a can include portions that are flexible 118a and portions that are less flexible 116a. The less flexible portions 116a can include at least one layer of a radiopaque material. It will be understood, however, that in other configurations portions 118a can be less flexible than portions 116a. Generally, the rails 104a and 106a can have generally uniform flexibility or multiple portions of differing flexibilities, whether or not one or more of such portions have the same of different flexibilities.

Alternatively, the rails can be replaced with, or in addition to, a continuous tube that surrounds the annular elements. As such, the continuous tube can contain the annular elements so as to form a double-layered endoprosthesis. In another configuration, the rails and/or connectors, spacing apart adjacent annular element can be substituted with one or more wires 119a. These wires 119a can extend between annular elements 101a and maintain the annular elements 101a in a coherent structure. These wires 119a can be radiopaque to increase the visibility of the endoprosthesis. These wires 119a can be interlaced or weaved with one or more elements of the annular elements 101a whether in a uniform or non-uniform manner.

Alternatively, and/or in combination thereof, one or more wires or braided material can be weaved, interlaced or otherwise coupled with the annular elements 101a and provide the desired increased visibility. In still another configuration, the annular elements 101a can be connected by way of one or more strut elements or crossbars, while the wires or braided material can be weaved, interlaced, or otherwise coupled to the endoprosthesis.

It will be understood that the above described structures that increase the visibility of the stent can be used with or without a multilayer structure and/or the inclusion of some other material wrapping around the annular elements 101a. Further, it will be understood that the rails, wires, and tubes can function as members that connect one or more annular elements to form the desired endoprosthesis.

The strut elements 102a can be comprised of at least an elbow 108a and a crossbar 110a, which can be similar as described above. Usually, the elbows 108a are high stress zones 112a and the crossbars 110a are low stress zones 114a. However, the endoprosthesis 100a can include other types of endoprosthetic and/or strut elements 102a as are well known in the art. Since the strut elements 102a can include high stress zones 112a, such zones can be comprised of multiple layers of materials that are configured to allow the endoprosthesis to close for deployment and open after implantation into a luminal passageway. Also, the low stress zones 114a can be fabricated from the same multiple layer material of the high stress zones 112a, or can be fabricated from a layer of a radiopaque material. Such flexible materials, radiopaque materials, and multilayered endoprosthetic elements are discussed in more detail below.

FIG. 3B is a side view illustrating a flattened portion of another embodiment of an endoprosthesis identified by reference number 100b. It should be understood that the illustrated portion of the endoprosthesis 100b can extend circumferentially and longitudinally as in FIG. 2. The endoprosthesis 100b is shown to include a plurality of strut elements 102b held together by couplings 126. The couplings 126 are disposed at connection elbows 111 and couple one elbow connection to another. Additionally, the strut elements 102b can be held together by one or more rails (not shown), as depicted in FIG. 3A. Alternatively, the strut elements 102b can be disposed within a tubular endoprosthesis (not shown).

The strut elements 102b can include at least an elbow 108b and a crossbar 110b, which can be similar as described above. Usually, the elbows 108b are high stress zones 112b and the crossbars 110b are low stress zones 114b. As shown, the strut elements 102b can include extended crossbars 128 that extend further than other crossbars 110a so as to extend between different connection elbows 111. The adjacent extended crossbars 128 can cooperate to couple adjacent annular elements 101b together through couplings or connection sections 126. Additionally, the endoprosthesis 100b can include other types of endoprosthetic and/or strut elements 102a as are well known in the art.

The portions of the strut elements 102b that are elbows 108b can be high stress zones 112b. Also, the portions of the strut elements 102b that are connection elbows 111 can be high stress zones 120. Additionally, the junction portions 124 of adjacent annular elements 101b can include a pair of extra-high stress zones 120. As depicted, the high stress zones 112b, high stress zones 120, and junction portions 124 tend to be circumferentially related and substantially orthogonal to the longitudinal axis of the endoprosthesis 100b. As such, the high stress zones 112b, extra-high stress zones 120, and junction portions 124 can include multiple layers of materials that are configured to allow the endoprosthesis 100b to be flexible so as to close for deployment and open after implantation into a luminal passageway. Such multiple layers of materials can include of flexible materials such as superelastic nitinol.

Further, the portions of the strut elements 102b that are low stress zones 114b (e.g., crossbars 110b and extended crossbars 128) can be of the same multi-layer material of the high stress zones 112b, or can include a layer of a radiopaque material. As shown, the extended crossbars 128 can include sections 112b that are circumferentially related with crossbars and substantially orthogonal to the longitudinal axis, sections 112b that are circumferentially related with elbows 108b, and sections 122 that are circumferentially related with other extended crossbars 128. Accordingly, the extended crossbars 128 can have sections with materials that are configured as low stress zones 114b, 122 separated by sections with materials configured as high stress zones 112b. Such configurations can take advantage of novel methods of preparing endoprostheses as described in more detail below. In any event, the flexible materials, radiopaque materials, and multilayered endoprosthetic elements are discussed in more detail below.

FIG. 3C is a side view illustrating a portion of an embodiment of an endoprosthesis 100c. The endoprosthesis 100c is shown to include one or more helical strut elements 102c. Accordingly, a single strut element 102c can extend from one end of the endoprosthesis 100c to the other end by being wound in a helical or spiral configuration. Optionally, the helical strut element 102c can be held in a spiral or helical configuration by at least a first rail 104c and second rail 106c (shown by dashed lines), one or more wires and/or braided material, as was described in connection with FIG. 3A. Briefly, the rails 104c, 106c, can include portions that are flexible 118c and portions that are less flexible 116c. The less flexible portions 116c can include at least one layer of a radiopaque material. Alternatively, a tubular endoprosthesis can be used in place of the rails so as to contain the strut elements 102c therein.

As with the endoprostheses 100a-b illustrated and described in connection with FIGS. 3A-3B, the endoprosthesis 100c can include strut elements 102c comprised of at least an elbow 108c and a crossbar 110c. Usually, the elbows 108c are high stress zones 112c, and the crossbars 110c are low stress zones 114c. However, the endoprosthesis 100c can include other types of endoprosthetic and/or strut elements 102c as are well known in the art that form helices or spirals. As before, since the strut elements 102c can include high stress zones 112c, such zones can include multiple layers of materials that are configured to allow the endoprosthesis to close for deployment and open after implantation into a luminal passageway. Also, the low stress zones 114c can include the same multiple layer material of the high stress zones 112c, or can include a layer of a radiopaque material. Such flexible materials, radiopaque materials, and multilayered endoprosthetic elements are discussed in more detail below.

FIG. 3D is a side view illustrating a portion of an embodiment of a braided, tubular endoprosthesis 100d. The endoprosthesis 100d is shown to include a plurality of braided elements 140, 142. As such, a plurality of first spiral elements 140 in a first orientation is braided with a plurality of second spiral elements 142 that are in a second orientation. Accordingly, the braid configuration provides for spaces 144 that are present between the first spiral elements 140 and the second spiral elements 142 while in open or deployed position. Additionally, the spaces 144 can close or collapse when the endoprosthesis 100d is in a collapsed or deployable orientation, and expand or fully open with the endoprosthesis is opened or deployed. Thus, the positioning of each of the plurality of first spiral elements 140 with respect to each of the plurality of second spiral elements 142 allows for the endoprosthesis to open and close. Moreover, any or all of the braided elements 140, 142 that are braided can include a multilayered body as described in more detail below.

Optionally, the braided elements 140, 142 and/or the endoprosthesis 100d can be held together by at least a first rail 104d and second rail 108d, shown by dashed lines. As such, the rails 108d, 104d can be radially disposed outwardly from the braided elements 140, 142 or the endoprosthesis 100d and any number of rails can be used. Alternatively, the rails 108d, 104d can be disposed internally (not shown) with respect to the braided elements 140, 142 or the endoprosthesis 100d. The rails 104d, 108d can be formed of a single material or a multi-layer material, as described in more detail below. Also, the rails 108d and/or 104d can include portions that are flexible 118d and portions that are less flexible 116d. The less flexible portions 116d can include at least one layer of a radiopaque material. Alternatively, the rails can be replaced by a tubular endoprosthesis that holds the braided elements 140, 142 in a tubular orientation, wherein such a tubular member can be placed upon the exterior of the braided elements 140, 142. Alternatively, the tubular member can be placed within the braided elements 140 or 142 or, when two or more tubular members are used, a tubular member can be placed within and/or upon the exterior of the braided elements 140, 142. These tubular members can be fabricated from a shape memory material and/or can be braided with the braided elements as the tubular members and the braided elements are drawn into the configuration for the endoprosthesis using known processing techniques and methods.

FIG. 3E is a side view illustrating a portion of an embodiment of a spiraled, tubular endoprosthesis 100e. The endoprosthesis 100e is shown to include a plurality of longitudinally adjacent spiral elements 150. As such, a plurality of longitudinally adjacent spiral elements 150 can be separated by spaces 152 that are present between each spiral element 150 while in open or deployed position. Additionally, the spaces 152 can close or collapse when the endoprosthesis 100e is in a collapsed or deployable orientation, and expand or fully open with the endoprosthesis is opened or deployed. Thus, the positioning of each of the longitudinally adjacent spiral elements 150 with respect to each other allows for the endoprosthesis to open and close. Moreover, any or all of the longitudinally adjacent spiral elements 150 can include a multilayered body as described herein.

Optionally, the spiral elements 150 and/or the endoprosthesis 100e can be held together by at least a first rail 104e and second rail 106e, shown by dashed lines. As such, the rails 106e, 104e can be radially disposed outwardly from the spiral elements 150 or the endoprosthesis 100e and any number of rails can be used. Alternatively, the rails 104e, 106e can be disposed internally (not shown) with respect to the spiral elements 150 or the endoprosthesis 100e. The rails 104e, 106e can be comprised of a single material or a multi-layer material, as described in more detail below. Also, the rails can include portions that are flexible 118e and portions that are less flexible 116e. The less flexible portions 116e can include at least one layer of a radiopaque material. Alternatively, the rails can be replaced by a tubular endoprosthesis that holds the spiral elements 150 in a tubular orientation, wherein such a tubular endoprosthesis can be place within and/or exterior to the spiral elements 150.

II. Endoprosthetic Elements

The endoprosthetic elements of the present invention can improve the overall structural integrity of an endoprosthesis or other medical devices. The endoprosthetic elements can include a plurality of layers in an amount and arrangement that can inhibit crack propagation, thereby improving the performance and reliability of the endoprosthesis. For example, any particular endoprosthetic element can include one or more adjacent layers at a boundary or junction. Optionally, the boundary or junction can be a bond that bonds the adjacent layers together. As such, the boundary or junction can serve to inhibit cracks from propagating from one layer to the next. Additionally, the positioning and size of the layers within the body of an element can serve to inhibit crack propagation because when a crack encounters a junction it cannot extend therethrough. FIGS. 4A through 5D illustrate exemplary cross-sectional profiles of strut members of an endoprosthesis fabricated in accordance with the present invention. As shown in FIGS. 4A through 4D the endoprosthesis is shown having a circular cross-sectional profile while in FIGS. 5A through 5D the endoprosthesis is shown having a square cross-sectional profile. It shall be understood that the cross-sectional profiles shown are merely exemplary and that the cross-sectional profile of the endoprosthesis may be any shape. As known to one of ordinary skill in the art, the cross-sectional profile of an endoprosthesis can be shaped by cutting, electro-polishing, grinding, etching and other known processes to produce any desired shape.

Further, the inclusion of radiopaque material as one or more of the layers can increase the visibility of endoprosthesis. FIG. 4A is an embodiment of an endoprosthetic element 200a that has a circular cross-sectional profile. The endoprosthetic element 200a can include a plurality of layers 206a-g disposed sequentially between a first surface 202a and a second surface 204a. Each layer 206 can be substantially flat and planar in shape, and can present in a range of thicknesses. Accordingly, the layers 206a-g can be sequentially positioned adjacent to one another within a plane of the element 200a. The individual layers 206a-g can be separated from one another by a series of junctions 208a-f, which are also substantially flat and planar. Usually, each junction 208 can have a negligible thickness or can be as thick as a layer 206 or vice-versa. It is further contemplated that layers may have a curved profile similar to the diameter of the endoprosthesis in any of the diameters between the crimped profile and an expanded profile.

FIG. 4B is an embodiment of an endoprosthetic element 200b that has a circular cross-sectional profile. The endoprosthetic element 200b can include a plurality of concentric layers 212a-c disposed sequentially between an external surface 210 and an inner core 216. Each layer 212 can be substantially tubular or cylindrical, and can be present in a range of thicknesses. Accordingly, the layers 212a-c can be sequentially, radially positioned adjacent to one another within a cross-sectional profile of the element 200b. The individual layers 212a-c and core 216 can be separated from one another by a series of concentric junctions 214a-c, which are substantially tubular or cylindrical so as to have substantially circular cross-sectional profiles. Usually, the junctions 214 can have negligible thickness or can be as thick as a layer 212 or vice-versa.

FIG. 4C is an embodiment of an endoprosthetic element 200c that has a circular cross-sectional profile. The endoprosthetic element 200c can include a plurality of matrix layers 218a-e, such as but not limited to matrix layers, disposed sequentially between a first surface 202c and a second surface 204c. Each layer 218 can be substantially flat and planar in shape, and can be present in a range of thicknesses. Accordingly, the layers 218a-e can be sequentially positioned proximate to one another within a cross-sectional profile of the element 200c. The individual layers 218a-e can be separated from one another by a bonding layer 220a-d, which are also substantially flat and planar. Usually, each bonding layer 220 can have negligible thickness or can be as thick as a layer 218, and are composed of a composition that is different from the matrix layers or vice-versa.

FIG. 4D is an embodiment of an endoprosthetic element 200d that includes a circular cross-sectional profile. The endoprosthetic element 200d can include a plurality of layers 222 disposed sequentially between a first surface 202d and a second surface 204d. Each layer 222 can be substantially planar, arcuate, bent, zigzag, wavy (as shown) or the like in shape, but have a surface 126 that is rough, wavy, uneven, or the like. Also, each layer 222 can be present in a range of thicknesses, and can be sequentially positioned adjacent to one another within a plane of the element 200d. The individual layers 222 can be separated from one another by a junction 224, which are substantially planar, but also can be rough, wavy, uneven, or the like. Usually, the junctions 224 have negligible thickness or can be as thick as a layer 222. The combination of surfaces 226 and junctions 224 that are rough, wavy, uneven, or the like can be configured so that different portions of adjacent layers 222 have varying distances of separation, which can increase the ability to inhibit crack propagation.

FIG. 5A is an embodiment of an endoprosthetic element 300a that has a polygonal cross-sectional profile. The endoprosthetic element 300a can include a plurality of layers 306a-e disposed sequentially between a first surface 302a and a second surface 304a. Each layer 306 can be substantially flat and planar in shape, and can be present in a range of thicknesses. Accordingly, the layers 306a-e can be sequentially positioned adjacent to one another within a plane of the element 300a. The individual layers 306a-e can be separated from one another by a series of junctions 308a-d, which are also substantially flat and planar. Usually, each junction 308 can have negligible thickness or can be as thick as a layer 306.

FIG. 5B is an embodiment of an endoprosthetic element 300b that has a square cross-sectional profile. The endoprosthetic element 300b can include a plurality of square layers 312a-b disposed sequentially between an external surface 310 and an inner core 316, wherein the inner core also has a square cross-sectional profile. Each layer 312a-b can be substantially square as depicted, or can be in any other polygonal shape, and present in a range of thicknesses. Accordingly, the layers 312a-b can be sequentially, radially positioned adjacent to one another within a plane of the element 300b. The individual layers 312a-b and core 316 can be separated from one another by a series of junctions 314a-b, which also can have substantially square cross-sectional profiles. Usually, each junction 314 can have negligible thickness or can be as thick as a layer 312.

FIG. 5C is an embodiment of an endoprosthetic element 300c that has a square cross-sectional profile. The endoprosthetic element 300c can include a plurality of layers 318a-d, such as but not limited to matrix layers, disposed sequentially between a first surface 302c and a second surface 304c. Each layer 318a-d can be substantially flat and planar in shape, and be present in a range of thicknesses. Accordingly, the layers 318a-d can be sequentially positioned proximate to one another within a plane of the element 300c. The individual layers 318a-e can be separated from one another by a bonding layer 320a-c, which are substantially flat and planar. Usually, each bonding layer 320 can be thin or can be as thick as a layer 318, and are composed of a composition that is different from the adjacent layers.

These bonding layers 320a-c can be considered as a boundary layer between adjacent layers. The structure of endoprosthetic element 300c can be formed using various techniques, such as, but not limited to, those described herein and those known to one skilled in the art in light of the teaching contained herein. For instance, and by way of example and not limitation, the layer-318a can be initially formed and then the bonding layer or boundary layer 320a-c deposited thereupon using one or more various techniques. The bonding layer or boundary layer 320a-c can be ground to the desired thickness before the layer 318b is deposited thereupon. This process can be continued for additional layers. Although the above process is described with respect to the configuration of FIG. 5C, it will be understood by one skilled in the art that it is also applicable to manufacture of any other endoprosthesis and can be combined with other manufacturing techniques, such as but not limited to those described herein.

FIG. 5D is an embodiment of an endoprosthetic element 300d that has a square cross-sectional profile. The endoprosthetic element 300d can include a plurality of layers 322a-c, 326a-b that each has a varying thickness. As depicted the endoprosthetic element 300c includes outer layers 322a-c and inner layers 326a-b that are a series of alternating wedges. Also, the outer layers 322a-c can be separated from the inner layers by 326a-b by a series of junctions 324a-d that form a zigzag boundary. For example, the layered endoprosthetic element 300d can have: a bottom outer layer 322a can be separated from a bottom inner layer 326a by a diagonally disposed junction 324a; the bottom inner layer can be separated from a middle outer layer 322b by a diagonally disposed junction 324b; the middle outer layer 322b can be separated from a top inner layer 326b by a diagonally disposed junction 324c; the top inner layer 326b can be separated from a top outer layer 322c by a diagonally disposed junction 324d. While one example of an endoprosthetic element 300d with alternating and interlocking layers 322, 326 has been illustrated, it is contemplated that other similar alternating and interlocking layers having various shapes and sizes can also be beneficial for inhibiting crack propagation.

The foregoing layers of the endoprosthetic elements can be of the same material or can be different materials. The use of the same materials separated by junctions can retain substantially the functionality of the material, and also provide junctions between the layers to inhibit crack propagation. The use of different materials in adjacent layers can be beneficial for imparting the characteristics of both types of materials to the endoprosthesis. Also, various types of bonding layers can be used to couple matrix layers to each other. Such bonding layers can be braided layers, spiral layers, laminate layers, adhesive layers, ceramic layers, polymer layers, chemical bonds, metallurgical bonds, or the like. As previously described, it can be advantageous to combine layers of radiopaque materials with layers of superelastic materials. Additionally, the materials for the different layers are described in more detail below. Moreover, the cross-sectional profile of an endoprosthetic element can be circular, oval, oblong, square, orthogonally rectangular, circumferentially rectangular, octagonal, polygonal, combinations thereof, or the like. Also, the cross-sectional profile can have edges and/or corners compatible with material devices, and/or placement into a body lumen. In addition, it is possible to use different materials for a junction layer, between two adjacent layers, with the junction layer having crack arresting properties. For instance, the junction layer can be fabricated from material that is less likely to crack than the adjacent layers. Also, it may be beneficial to have multiple junction layers to strengthen the bond and arrest cracks)

The size or thickness of the layers across a cross-sectional profile of an endoprosthetic element can be modulated to correspond with the width, thickness, and/or cross-sectional profile as well as the functionality of the endoprosthetic element. That is, crossbars may have different multilayered cross-sectional profile configurations compared to an elbow. As such, the type of cross-sectional profile can be tailored for low stress zones or for high stress zones. For example, stents having crossbars with a width or diameter from about 5 micron to about 500 micron can include a plurality of layers that each have a dimension with a selected percentage of the width or diameter across a given width, thickness and/or cross-sectional profile. As such, the size of the individual layers across a given width, thickness, and/or cross-sectional profile can be tailored to provide sufficient structural integrity, inhibition of crack propagation, and/or radiopacity Moreover, it should be recognized that different layers can have different thickness than the other layers. In one configuration, an endoprosthetic element can have a width, thickness, or cross-sectional profile that includes at least two layers. The two layers across the endoprosthetic element can each have a thickness or width that can partition the element into at least a first portion and a section portion.

In another configuration, the multiple layers include a member having an outer body that is filled with another material. For example, the concentric cross-sectional profiles of FIGS. 4B and 5B can be representative of an outer body being filled with another material. While the concentric cross-sectional profiles of FIGS. 4B and 5B show multiple inner layers that are filled within an outer body, it should be recognized that an outer body can be filled with a single material, thereby forming a core and outer body.

Additionally, the diameter or width of each layer that is situated at a given width, thickness, and/or cross-sectional profile can be varied to correspond with size limitations of the endoprosthetic element. For example, endoprosthetic elements having a large width, thickness, and/or cross-sectional profile can have layers with larger diameters or widths.

Additionally, the use of multiple layers of different materials connected by boundaries or junctions can provide more crack-resistant endoprostheses. Also, it can be desirable for the multilayered material to substantially stable so as to not delaminate. As such, the multilayered material can be configured to include adjacent layers that are bound together in a manner that exhibits good anti-delaminating properties under expansion or stress.

Also, the multilayered endoprosthesis can be configured to have different strength and flexibility at different locations or at different endoprosthetic elements. The different strength and flexibility can be tailored by selection of types of materials and numbers of layers as well as by varying the thickness. For example, it may be beneficial to have high stress zones having a greater thickness than a low stress zone that has a smaller thickness.

Moreover, the endoprosthetic elements in accordance with the present invention can also include crack-inhibiting features such as recesses, apertures, holes, particles, and/or fibers. The crack-inhibiting features can be useful for inhibiting crack formation and/or crack propagation and/or fatigue-induced catastrophic failure. Additional information regarding the amount distribution, characterization and the like for such features can be reviewed in the incorporated references.

A mechanical bond between the multiple layers of Nitinol may be utilized to form the composite structure according to the present invention. Though, it may be desirable that a metallurgical bond be formed where diffusion of the material elements takes place between the multiple layers of the materials as the structure forming the endoprosthesis is fabricated. This metallurgical bond can be formed through the application of pressure and heat to the materials, as described below.

III. Prosthetic Composition

The endoprostheses of the present invention can be made of a variety of materials. This can include an endoprosthesis having multiple layers of the same material as well as multiple layers of two or more different materials. The materials can be selected according to the desired structural performance and/or biological characteristics. Multiple layers of materials can be beneficial for inhibiting crack propagation, especially at locations that are more susceptible to high flexing like high stress zones. For example, materials such as Ti3Al2.5V, Ti6Al4V, 3-2.5Ti, 6-4Ti and platinum may be particularly good choices for adhering to a flexible material, such as, but not limited to, Nitinol and providing good crack arresting properties. Also, multiple layers can be useful for applying radiopaque materials to an endoprosthesis, especially at low stress zones. For example, types of materials that are used to make a multilayered endoprosthesis of the present invention can be selected so that the endoprosthesis is capable of being collapsed during placement and expanded when deployed. Usually, the endoprosthesis can be self-expanding, balloon-expandable, or can use some other well-known configuration for deployment. For purposes of illustration and not limitation, reference is made generally to self-expanding embodiments and balloon expandable embodiments of the endoprosthesis of the present invention; however, other types of endoprostheses can be configured to be multilayered in accordance with the present invention.

Self-expanding embodiments of an endoprosthesis can include at least one layer made from any of a variety of known suitable materials, such as a shaped memory material ("SMM"). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys ("SMA"), such as metal alloys, or shape memory plastics ("SMP"), such as polymers.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened compacted, and placed into various contortions by the application of requisite forces; however, after the forces are released the SMA can be capable of returning to the memory shape. The main types of SMAs are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy. Typically, the nitinol and elgiloy alloys can be more biocompatible, but have superior mechanical characteristics in comparison with the copper-based SMAs. The temperatures at which the SMA changes its crystallographic structure are characteristic of the alloy, and can be tuned by varying the elemental ratios.

For example, it can be preferable for the primary material of at least one layer or all layers of an endoprosthesis to be of a NiTi alloy that forms superelastic Nitinol. In the present case, Nitinol materials can be trained to remember a certain shape, straightened in a shaft, catheter, or other tube, and then released from the catheter or tube to return to its trained shape. Also, additional materials can be added to the nitinol depending on the desired characteristic.

An SMP is a shape-shifting plastic that can be fashioned into at least one layer of an endoprosthesis in accordance with the present invention. Also, it can be beneficial to include at least one layer of an SMA and at least one layer of an SMP to form a multilayered body. When an SMP encounters a temperature above the lowest melting point of the individual polymers, the blend makes a transition to a rubbery state. The elastic modulus can change more than two orders of magnitude across the transition temperature ("Ttr"). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

For example, Veriflex™, the trademark for CRG's family of shape memory polymer resin systems, currently functions on thermal activation which can be customizable from −20° F. to 520° F., which allows for customization within the normal body temperature. This allows an endoprosthesis having at least one layer of Veriflex™ to be inserted into a delivery-catheter. Once unrestrained by the delivery shaft, the body temperature can cause the endoprosthesis to spontaneously and automatically take its functional shape.

An endoprosthesis having at least one layer made of a SMM or suitable superelastic material and other suitable layers can be compressed or restrained in its delivery configuration within a delivery device using a sheath or similar restraint, and then deployed to its desired configuration at a deployment site by removal of the restraint, as is known in the art. An endoprosthesis made of a thermally-sensitive material can be deployed by exposure of the endoprosthesis to a sufficient temperature to facilitate expansion, as is known in the art.

Balloon-expandable endoprosthesis embodiments can have at least one layer made of any of a variety of known suitable deformable materials, including stainless steel, silver, platinum, tantalum, palladium, cobalt-chromium, tungsten alloys or other known biocompatible materials.

For delivery, the balloon-expandable endoprosthesis having multiple layers of suitable materials can be mounted in the delivery configuration on a balloon or similar expandable member of a delivery device. Once properly positioned within the body lumen at a desired location, the expandable member can be expanded to expand the endoprosthesis to its deployed configuration as is known in the art.

Also, balloon-expandable endoprosthesis embodiments can optionally have at least one layer that is made of a suitable biocompatible polymer in addition to or in place of a suitable metal. The polymeric endoprosthetic layers can include biodegradable or bioabsorbable materials, which can be either plastically deformable or capable of being set in the deployed configuration. If plastically deformable, the material can be selected to allow the endoprosthesis to be expanded in a similar manner using an expandable member so as to have sufficient radial strength and scaffolding and also to minimize recoil once expanded. If the polymer be set in the deployed configuration, the expandable member can be provided with a heat source or infusion ports to provide the required catalyst to set or cure the polymer. Alternative known delivery devices and techniques for self-expanding endoprostheses likewise can be used.

Additionally, a self-expanding embodiment of an endoprosthesis can have at least one layer that is comprised of a biocompatible material capable of expansion upon exposure to the environment within the body lumen. The layer can be a layer on that forms the external surface or interior surface of the endoprosthesis. Examples of such biocompatible materials can include a suitable hydrogel, hydrophilic polymer, biodegradable polymers, bioabsorbable polymers. Examples of such polymers can include poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like. For example, a self-expandable endoprosthesis can be delivered to the desired location in an isolated state, and then exposed to the aqueous environment of the body lumen to facilitate expansion.

Furthermore, the multilayered endoprosthesis can include at least one layer that is of a ceramic material. The ceramic layer can be an exterior layer of a biocompatible ceramic which optionally can be porous. Alternatively, the ceramic layer can be an internal layer that is used as a bonding layer between the two adjacent layers. Examples of suitable ceramic materials can include, but are not limited to, hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of an endoprosthesis or layer thereof.

The multilayered endoprosthesis can optionally include at least one layer that is radiopaque to increase visibility after placement. Optionally, the layer of the radiopaque material is disposed at low stress zones that are not as susceptible to cracking as high stress zones that bend and flex. The radiopaque materials can include, but are not limited to, platinum, tungsten, silver, stainless steel, gold, tantalum, bismuth, barium sulfate, or a similar material.

In one configuration, each layer of the endoprosthesis is fabricated from Nitinol, though it is contemplated that each layer may include a different chemical composition and/or different metals. These layers can be bonded together using processes described herein or others known to those skilled in the art in light of the teaching contained herein. It is recognized that other biocompatible materials can be substituted for at least one of the Nitinol layers. It is further contemplated that an adhesion layer can be disposed between the layers of the Nitinol material, which will act as a barrier for crack propagation. Further still, it is contemplated that the composite tubular member may be constructed of more than two layers. For example, it can be possible to form the composite tubular member from a plurality of thin layers, wherein each layer is concentrically arranged, whereby the increased number of layers can provide more crack-resistance or reduced crack propagation and/or increased radiopacity.

Additionally, other well-known delivery devices and techniques for a self-expanding endoprosthesis can be used. For example, prior to crimping of the self-expanding endoprosthesis for loading into a delivery system, the endoprosthesis may be coated with a lubricant, such as silicone oil, to reduce force between the endoprosthesis and the crimping device and additionally to reduce forces of disposing the endoprosthesis in a delivery device. Additionally, the lubricant may reduce deployment force thereby increasing accuracy of endoprosthesis placement within a patient. The lubricant may be introduced prior to, during, or after the crimping or loading process.

A. Biodegradable Coating Layers

It is further contemplated that the external surface and/or internal surface of the endoprosthesis (e.g., exterior and luminal surfaces) can be coated with another material having a composition different from the primary endoprosthetic material. As used herein, the term "coating" is not meant to refer to a layer, but is merely a material coated onto an exterior layer of an endoprosthetic body. The use of a different material to coat the surfaces can be beneficial for imparting additional properties to the endoprosthesis, such as providing radiopaque characteristics, drug-reservoirs, and improved biocompatibility.

In one embodiment, all surfaces of an endoprosthesis can be coated with a biocompatible material. Such coatings can include hydrogels, hydrophilic and/or hydrophobic compounds, and polypeptides, proteins or amino acids or the like. Specific examples can include polyethylene glycols, polyvinylpyrrolidone ("PVP"), polyvinylalcohol ("PVA"), parylene, heparin, phosphorylcholine, and the like.

The coatings can also be provided on the endoprosthesis to facilitate the loading or delivery of beneficial agents or drugs, such as therapeutic agents, pharmaceuticals and radiation therapies. As such, the endoprosthetic material and/or holes can be filled and/or coated with a biodegradable material. For example, the biodegradable polymer composition can include at least one of poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like.

Accordingly, the biodegradable material can contain a drug or beneficial agent to improve the use of the endoprosthesis. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof. It will be understood by one skilled in the art that various other suitable drugs or beneficial agents can be included.

In addition to the above-identified coatings, the external surfaces of an endoprosthesis can be coated with a degradable material that is configured to be responsive to radio-frequency ("RF") energy or ultrasonic energy. As such, the degradability of the filling and/or coating can be altered in response to applied RF energy. Alternatively, the external surfaces of an endoprosthesis can include a coating of polytetrafluoroethylene ("PTFE"), expanded PTFE ("ePTFE"), Dacron®, woven materials, cut filaments, porous membranes, harvested vessels and/or arteries, or others such materials to form a stent graft prosthesis. Similarly, a medical device, such as a valve, a flow regulator or monitor device, can be attached to the endoprosthesis, such that the endoprosthesis functions as an anchor for the medical device within the body lumen.

In one embodiment, different external surfaces of an endoprosthesis, such as low stress zones, can be coated with functional layers of an imaging compound or radiopaque material. The radiopaque material can be applied as a layer at low stress and/or the high stress zones of the endoprosthesis. Also, the radiopaque material can be encapsulated within a biocompatible or biodegradable polymer and used as a coating. For example, a suitable radiopaque material can be, but is not limited to, palladium platinum, tungsten, silver, stainless steel, gold, tantalum, bismuth, barium sulfate, or a similar material. The radiopaque material can be applied as layers on selected surfaces of the endoprosthesis using any of a variety of well-known techniques, including cladding, bonding, adhesion, fusion, deposition or the like.

B. Matrix With Dispersed Fibrous Material

In addition to the foregoing compositions, a fibrous material can also be included within the matrix of an individual layer of an endoprosthesis. As such, any layer of the foregoing compositions can be impregnated and/or encapsulated with a suitable fibrous material. Also, a fibrous material can extend across multiple layers. The fiber-reinforced materials can range in composition depending on the desired characteristics, and can be included in various amounts, distributions, and orientations. Additionally, the size of the fiber can be modulated from short fibers to long fibers, as well as continuous fibers. The fibers can function similar to the use of multiple layers by providing dislocations within the endoprosthetic matrix that inhibit crack formation and/or crack propagation and/or fatigue-induced catastrophic failures. As such, the foregoing discussions related to the use of multiple layers can be combined and applied here to the use of fiber-reinforced endoprosthetic layers. While the following discussion is directed to fibers, it should be recognized that such discussion can also be applied to particles which can be imbedded within the individual layers of a multilayered material to inhibit crack propagation. Additional information regarding fibers being dispersed through a matrix of a layer can be found in the incorporated reference "CRACK/FATIGUE RESISTANT ENDOPROSTHESIS" with Randolf Von Oepen as inventor, filed herewith on Mar. 13, 2006.

Various types of fibers may be used in order to obtain specific characteristics. For example, the endoprosthetic compositions can include naturally occurring organic fibers extracted from hemp, cotton, plant leaves or stems, hardwoods, softwoods, or the like, fibers made from organic polymers, examples of which include polyester and nylon (i.e., polyamide), and/or inorganic fibers, examples of which include glass, graphite, silica, silicates, microglass made alkali resistant using borax, ceramics, carbon fibers, carbides, metal materials, and the like. The preferred fibers, for example, include glass fibers, woolastanite, abaca, bagasse, wood fibers (e.g., soft pine, southern pine, fir, and eucalyptus), cotton, silica nitride, silica carbide, silica nitride, tungsten carbide, and Kevlar; however, other types of fibers can be used.

The various above-described fibers can be mixed together with the endoprosthetic matrix of an individual layer by well-known techniques. As such, the fibers and metal or polymer components can be sufficiently mixed together in order to obtain a composition having fibers homogenously distributed therethrough.

IV. Method of Making Endoprostheses

Various different manufacturing techniques may be used for fabrication of the multilayered endoprosthesis of the present invention. For example, in configuration, the endoprosthesis can be formed from a hollow tube having concentric layers of suitable materials using a known technique, such as laser cutting, EDM, milling, chemical etching, hydro-cutting, and the like. Such layers can be formed by sequential deposition through a cladding process such as vapor deposition, electroplating, spraying, or similar processes. Alternatively, the hollow tube can be fabricated using drawing, swaging, sintering, or welding techniques. Also, various other processes can be used such as those described below and well known in the art.

Alternatively, the endoprosthesis can be fabricated from a sheet of suitable material, where the sheet is rolled or bent about a longitudinal axis into the desired tubular shape. Additionally, either before or after being rolled into a tube, the material can be shaped to include endoprosthetic elements by being shaped with well-known techniques such as laser-cutting, milling, etching or the like. If desired, the lateral edges of the structure can be joined together, such as by welding or bonding, to form a closed tubular structure, or the lateral edges can remain unattached to form a coiled, rolled sheet or open tubular structure. Such fabrication techniques are described in more detail below.

A. Sintering

A method of making an endoprosthesis in accordance with the present invention can include sintering sinterable particles to provide a sintered article having the shape of the endoprosthesis or a single layer of an endoprosthesis. The sintering can be conducted in molds that form a single layer of a selected material or molds that receive distinct layers of different sinterable materials so that a body having various distinct layers can be produced. Alternatively, multiple sintered bodies that are sequential in size can be prepared, inserted into each other, and bonded together by well-known methods such as drawing, brazing, or sintering optionally with additional materials between those layers. As such, a single body can form the endoprosthesis.

In one embodiment, the multilayered sintered body can be obtained from a multilayered green body, i.e., a part in an uncured or unfired state, prepared by molding a mixture of sinterable particles with or without a binder into the shape of an endoprosthesis or body intermediate. In one aspect, separate green bodies each having a uniform composition can be molded and layered together so that adjacent layers have different compositions. In the instance multiple layers of sinterable particles are molded and layered together it can be preferable for such individual layers to be comprised of sinterable particles held together with a suitable binder. In another aspect, a single mold can have sinterable particles sequentially injected therein so as to form multiple distinct layers or layers that are intermingled at each interface. Also, sequentially injecting different layers can be performed with sinterable particles that are combined with a binder. In any event, sintering a molded green body that has the shape of an endoprosthesis can provide a sintered body that can function as an endoprosthesis with no or minimal further processing. Alternatively, after the green body has been formed in the mold and sintered into a hardened endoprosthesis, the process can include shaping the sintered body with a stream of energy and/or matter in order to obtain a desired shape. Thus, sintering a multilayered green body in a mold can result in an endoprosthesis that is either ready for use, or requires additional processing or finishing.

When the multilayered green body is sintered, the volume can shrink as the porosity decreases and the density increases, especially when the sinterable particles are held together with a binder. This can happen as the majority of the binder is melting and/or evaporating so as to draw the individual sinterable particles closer together. As such, the green body can be fabricated, molded, and/or shaped to be larger than the resultant sintered article in order to accommodate for the volume lost during sintering. The volume decrease between the size of a green body and the size of a sintered article can range from about 10% to about 35%, about 12% to about 30%, or about 15% to about 25%; however, a typical volume decrease can be about 20%. However, in instances where no binder is used to hold the sinterable particles together, sintering may result in negligible volume change.

Additionally, the sintered body can be shaped into an endoprosthesis as described herein. Also, the endoprosthesis can be further processed after sintering and/or shaping such as by grinding, sanding, or the like to provide enhanced surface characteristics.

B. Filled Tubular Elements

In one embodiment, an endoprosthetic element can have an outer tube and at least one core. For example, the cross-sectional profiles of elements having concentric layers shown in FIGS. 4B and 5B can be prepared by forming an outer tube, such as 212a and/or 312a, that is filled with a core material, such as 216 or 316, or internal layers, such as 212b, 212c, or 312b, 312c, being disposed between the outer tube and the core. Also, the core can have longitudinally-sequential sections. This can allow for one portion of the tube and core to have one functionality, such as flexibility, and for another portion of the tube and core to have another functionality, such as radiopacity.

FIG. 6A is a schematic representation of a body 400a that can be used to form a portion of an endoprosthesis, such as an annular element, crossbar, elbow, connector, or the like. As such, the body 400a can be in the form of an elongate cylinder 402 that has an outer tube 401a that is substantially cylindrical with an internal lumen extending from a first end 404a to a second end 406a. The lumen can be filled with alternating sections 408a, 410a of different materials. As shown, the section 408a can be configured to be a flexible section for use as an endoprosthetic element at a high stress zone, such as an elbow. Also, the section 410a can be configured to be more rigid or less bendable section for use as an endoprosthetic element at a low stress zone, such as a crossbar or connector.

FIG. 6B is a schematic representation of an annular body 412 that can be used to form an annular member or annular portion of an endoprosthesis. Accordingly, the annular body 412 can be obtained by bending the elongate cylinder 402 of FIG. 6A into a circle. As such, the first end 404a and second end 406a of the elongate cylinder 402 or FIG. 6A can be coupled, welded, brazed, or otherwise joined together so as to form an intersection the first end 404b and second end 406b of the annular body 412. Alternatively, an intermediate coupling or member can be used to connect the first end 404a and the second end 406a. Also, the outer tube 401b can optionally include different circumferentially-sequential sections for use as different portions of the endoprosthesis. As shown, the section 408b can be configured to be a flexible section, and the section 410a can be configured to be more rigid or less bendable section. Alternatively, the elongate cylinder 402 of FIG. 6A can be bent into a spiral or helix in accordance with the embodiments of endoprostheses shown in FIGS. 3C-3E.

FIG. 6C is a schematic representation of a bent annular body 417 that can be used to form an annular member or annular portion of an endoprosthesis. Accordingly, the bent annular body 417 can be obtained by bending selected sections of the annular body 412 of FIG. 6B into a warped or wavy ring (e.g., a ring that has multiple circumferential bends in the longitudinal direction). Also, the outer tube (not shown) can include different circumferentially-sequential sections for use as different portions of the endoprosthesis, which is shown by section 407 being an elbow, and the adjacent section 409 being a crossbar. As shown, the section 408c can be configured to be a flexible section (e.g., elbow section 407), and the section 410c can be configured to be more rigid or less bendable section (e.g., crossbar 409).

FIG. 6D is a schematic representation of an endoprosthesis 414 comprised of a plurality of bent annular bodies 416. The bent annular bodies 416 can be separated by spaces 418 and bonded together with connectors 420. Alternatively, the bent annular bodies 416 can be joined by couplings as show herein. As shown, the section 408d, which can be can be configured to be a flexible section (e.g., elbow section 407), can be located at a high stress zone 412. Additionally, the section 410d, which can be configured to be more rigid or less bendable section (e.g., crossbar 409), can be located at a low stress zone 414.

C. Rolled Sheets

FIG. 7A is a schematic representation of a body 400b that can be used to form a substantially tubular endoprosthesis. As such, the body 400b can include a sheet 422 defined by a first end 424 opposite a second end 426, and a first side 423 opposite a second side 425. Also, the sheet 422 can include a top surface 421 opposite a bottom surface (not shown). The sheet can have a plurality of discrete sections 427, 428, which can be sections that are coupled together or sections defined by the layers that form the multilayered material. As such, each distinct section 427, 428, can have a composition that is different from the other layers. As shown, the section 428 can be configured to be a flexible section for use as an endoprosthetic element at a high stress zone, such as an elbow. Also, the section 427 can be configured to be more rigid or less bendable section for use as an endoprosthetic element at a low stress zone, such as a crossbar or connector. Also, it should be recognized the sheet 422 is not drawn to scale and any of the dimensions can be varied.

FIG. 7B is a schematic representation of an endoprosthesis 430 in the form of a tubular body 434 prepared from the sheet 422 of FIG. 7A. Accordingly, the sheet 422 can be rolled into a tubular body 434 in a manner such that the first side 423 is circumferentially disposed adjacent with and coupled to the second side 425. The first side 423 and the second side 425 can be coupled together either directly or by use of a secondary material or coupling, such as know to those skilled in the processing art. For instance, the first side 423 and the second side 425 can be coupled together through welding, brazing, intermediate material or element, or the like. As such, the first end can be separated from the second end 426 by a lumen 437 defined by one of the top side 421 or bottom side of the sheet 422. After the tubular body 434 is formed, it can be cut or shaped to have endoprosthetic elements, such as crossbars 430, elbows 428, and connectors 432.

As shown, the sections 428 of FIG. 7A can form annular elements that correspond with high stress zones 435. As such, the high stress zones 435 of the tubular body 434 can be shaped into elbows 428 and connectors 432. Additionally, the section 427 of FIG. 7A can form annular elements that correspond with low stress zones 433. As such, the low stress zones 433 of the tubular body 434 can be shaped into crossbars 430. Alternatively, various other configurations of shapes of endoprosthetic elements can be prepared from a tubular body 434 having discrete sections that correlate with high stress zones 435 and low-stress zones 433.

In another embodiment, the sheet 422 of FIG. 7A can be rolled into a tubular body similar to the tubular body 414 shown in FIG. 6D. As such, the sheet 422 can be rolled in a manner such that the first end 424 is circumferentially disposed adjacent and coupled to the second end 426. As such, the first side 423 can be separated from the second side 425 by a lumen defined by one of the top side 421 or bottom side of the sheet 422. Additionally, various endoprosthetic elements can be shaped into such a tubular body as described herein or well known in the art.

FIG. 8A is a schematic representation of a body 400c that can be used to form a substantially tubular endoprosthesis having radiopaque ends. As such, the body 400c can include a sheet 442 defined by a first end 444 opposite a second end 446, and a first side 443 opposite a second side 445. Also, the sheet 442 can include a top surface 441 opposite a bottom surface (not shown). The sheet can have a main section 448 that is of a multilayered material, and end sections 450 that are of a multilayered material having at least one radiopaque layer. As shown, the light main section 448 can be configured to be a flexible section and can be shaped into any endoprosthetic element.

FIG. 8B is a schematic representation of a tubular body 452 prepared from the sheet 442 of FIG. 8A. Accordingly, the sheet 442 can be rolled into a tubular body 452 in a manner such that the first side 443 is circumferentially disposed adjacent and coupled to the second side 445. As such, the first end 444 can be separated from the second end 446 by a lumen 451 defined by one of the top side 441 or bottom side of the sheet 422.

FIG. 8C is a schematic representation of an embodiment of an endoprosthesis 454 prepared from the tubular body 452 of FIG. 8B. The tubular body 452 can be cut and shaped by any process described herein and well known in the art. Such shaping can result in endoprosthetic elements exemplified by crossbars 456 and connection elbows 458 being fabricated from the main section 448. Also, the shaping of the tubular body 452 can have the end sections 450 being cut into any shape that forms radiopaque markers 460.

FIG. 9A is schematic representation of an embodiment of an endoprosthesis 470a that can be processed to include radiopaque markings. As such, the endoprosthesis 470a can include a plurality of annular elements 472 that are connected together at connections 478, which can be any described herein or well known in the art. Also, the annular elements 472 can include crossbars 474 that are interconnected by elbows 476. In any event, the endoprosthesis 470a can be fabricated from a multilayered material.

FIG. 9B is a schematic of an embodiment of an endoprosthesis 470b that can be fabricated to include radiopaque markings 480. As such, a plurality of radiopaque markers 480 can be coupled to either end 484 of the endoprosthesis 470b. For example, the radiopaque markers 480 can be coupled to the end 484 via a coupling 482. Such a coupling can be a weld, braze, or the like. Alternatively, the radiopaque marker 480 can be prepared from a ceramic that is formed onto the end 484 of the endoprosthesis 470b. Alternatively, the radiopaque members can be mounted in accordance with the description related to FIGS. 1a-1c.

D. Braided Elements

In one embodiment, an endoprosthesis can be manufactured to include a multi-layered body, wherein one layer of a braid material. Optionally, the individual braid elements can be multilayered, can form multiple layers at the intersections of the counterclockwise and/or clockwise braid elements, or a braided tube can be processed with another tube to form multiple layers. In any event, the use of a braided material having braided elements that cross each other can provide for inhibited crack propagation. In part, a crack in one braid element may not start or propagate through another braid element. Additionally, the orientation of the braid elements of a braided tube can inhibit crack propagation from adjacent, concentric tubes. Selecting the braided material from a radiopaque material can also increase the visibility of the endoprosthesis.

A braided tube can be prepared as shown in FIG. 2D or the like. The process for preparing a braided tube is well known in the art of tube manufacturing. Additionally, the braided tube can be processed with optional rails bonded thereto. Also, the braided tube can be placed concentrically with another tube so that a lamination-like process forms a single tube therefrom. Such a lamination-like process can be performed by drawing the tubes together as described in more detail below. Briefly, a braided tube can be concentrically placed within and/or outside of another tube(s), which can also be of a braided tube. The concentric tubes can then be drawn together and heat set. Also, another material that can act to braze or weld the adjacent tubes can be disposed therebetween before the drawing and heat setting.

E. Drawing Concentric Tubes

In one embodiment, a multilayered endoprosthesis can be prepared by a drawing process that draws two or more distinct concentric tubes into a single tube having two or more layers. Additionally, such a drawing process can combine multiple concentric tubes into a single multilayered tube. The drawing process can be configured to produce junctions separating adjacent layers or bonds that bond adjacent layers. As such, the concentric tubes can be drawn together and progressively reduced in cross-sectional profile until the desired size and residual clamping stress is attained.

Accordingly, a metallurgical bond can be prepared with elements of each sequentially-concentric tube diffusing together and bonding so as to form a strong metallurgical bond. Such a metallurgical bond can be achieved by applying significant pressure and heat to the tubes. As such, a metallurgical bond can form a diffusion layer at the interface between concentric tubes (i.e., layers). The characteristics of these diffusion layers can be controlled by the proper heat treatment cycle. In part, this is because the heat treatment, temperature, and time of processing can control the rates of transfer of the diffusing elements that produce the diffusion layers. Also, the pressure at the interface between layers can be developed so as to result in the residual radial clamping stress in the tube after drawing.

In one example of this process, an outer tube of Nitinol, a middle tube of tantalum, and an inner tube of nitinol can be arranged to form the composite structure. The multilayered material can be produced to result in bonding between the layers so as to achieve a residual clamping stress of at least about 50 p.s.i. Accordingly, the annealing process can be performed within a limited range of time and temperatures. For example, the lower limit can be at least about 1550oF for at least six minutes, and the upper limit can be less than about 1850oF for less than 15 minutes.

In another embodiment, a metallic interleaf layer can be placed between separate tubes so as to bond the tubes together and form a multilayered material. The multiple tubes separated by the metallic interleaf layer can be drawn together and progressively reduced until the desired cross-sectional profile and residual clamping stress is attained, as described above. The drawn tubes can be heat-treated to form a diffusion bond between the separate layers. As such, the metallic interleaf layer can enhance the diffusion rate or type of diffusing atoms that are transported across a diffusion region between one layer and the interleaf layer.

In one embodiment, a multilayered sheet can be prepared to have separate layers of different materials or the same material. For example, the multilayered sheet can have a top layer of Nitinol, a middle layer of tantalum, and a bottom layer of Nitinol. The sheet can be prepared by metallurgically bonding the layers prior to a deep drawing process, which is well known in the art. During the deep drawing process, the sheet can be placed over a die and forced into the die, such as by a punch or the like. A tube having a closed end and a defined wall thickness can be formed in the die. This process can be repeated using a series of dies that have progressively decreasing diameters until a multilayered tube is formed having the desired diameter and wall thickness. For certain material combinations, intermediate heat treatments can be performed between the progressive drawing operations to form a multilayered material that is resistant to delaminating. Once a multilayered tube of desired thickness and dimensions has been formed, the closed end and the curved edges can be cut off. Then, the tube can be heat treated as described above until proper inter-metallic bonds are formed between the layers.

F. Additional Processing

In one embodiment, the foregoing drawing process can be performed to prepare tubes that can be formed into separate annular elements in accordance with FIGS. 6A-6C. As such, a drawn tube having a narrow diameter can be sequentially filled with different materials as loose powders and/or hardened rods. The loose powders can be hardened together and with the outer tube by sintering or other process.

Conversely, a suitable material of construction-can be applied selectively to a substrate to define the desired pattern of the endoprosthesis structure, and then the substrate can be removed. Other methods of manufacture also can be used for the endoprosthesis of the present invention, such as bending toroidal rings or elongate lengths of wire into appropriately shaped members, corresponding to each annular element, and then joining the appropriately shaped members together at connection locations by a welding or bonding technique or the like. If an SMM is used, such as Nitinol, the fabricated structure can be heat treated on a mandrel or the like using known techniques to establish the desired endoprosthesis shape and dimensions at a predetermined temperature (e.g., when above austenitic transition temperature).

An additional step of passivation can be performed during the manufacturing stage of the endoprosthesis in order to form a homogeneous oxide layer for corrosion resistance. The passivation process may be performed prior to installation of the markers in accordance with the present invention or it may be performed after installation of the radiopaque markers. Alternatively, multiple passivation processes may be performed, once prior to application of the markers, and again after insertion of the markers.

As originally shaped and/or fabricated, the endoprosthesis can correspond to its delivery configuration, to a deployed configuration, or to a configuration therebetween. However, the endoprosthesis can be fabricated with a configuration at least slightly larger than the delivery-configuration. In this manner, the endoprosthesis can be crimped or otherwise compressed into its delivery configuration in a corresponding delivery device.

In another preferred embodiment, the endoprosthesis can be originally fabricated from a tube having a diameter corresponding to the deployed configuration. In this manner, the longitudinally-free portions of the annular elements (e.g., elbow or foot not at a connection location) and circumferentially-free portions (e.g., the toe and/or heel portion of the foot extensions) can be maintained within the general cylindrical shape (e.g., diameter) of the endoprosthesis when deployed, so as to avoid such portions from extending radially inward when in the deployed configuration. The endoprosthesis can be designed to match the target vessel in which the endoprosthesis is to be deployed. For example a stent can be provided with an outer diameter in the deployed configuration ranging from about 1 mm for neurological vessels to about 25 mm for the aorta. Similarly, a stent can be provided with a length ranging from about 5 mm to about 200 mm. Variations of these dimensions will be understood in the art based upon the intended application or indication for the endoprosthesis.

As previously noted, the geometry of each component of the endoprosthesis or endoprosthetic element, such as the width, thickness, length and shape of the strut elements, crossbars, connectors, elbows, foot portions, ankle portions, toe portions, heel portions and the like can be selected to obtain predetermined expansion, flexibility, foreshortening, coverage scaffolding, and cross-sectional profile characteristics. For example, longer crossbars and/or connectors can promote greater radial expansion or scaffolding coverage. The phase difference or circumferential alignment between adjacent annular elements likewise can be altered to control coverage and flexibility. Similarly, the number and placement of connection locations and, if present, the connectors, between longitudinally-adjacent annular elements can be selected to obtained the desired flexibility of the endoprosthesis. The number of elbows and/or foot extensions between connection locations also can be varied to achieve desired performance characteristics.

G. Shaping

Accordingly, an endoprosthetic material can be shaped by various methods as described in more detail below. Such shaping techniques can utilize streams of energy and/or streams of matter in order to impart shapes into the endoprosthetic material. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the endoprosthetic material to form endoprosthetic element and/or holes therein.

In one embodiment, a stream of energy can cut, shape, and/or form a tube into an endoprostheses by generating heat at the site where the stream intersects the material, as is well known in the art. The thermal interaction can elevate the local temperature to a point, which can cut, melt, shape, and/or vaporize portions of the endoprosthetic material from the rest of the material.

Accordingly, one embodiment of the stream-cutting apparatus can operate and shape the endoprosthetic material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one embodiment, by knowing the thermal properties of the endoprosthetic material, precise energy requirements can be calculated so that the thermal beam provides the appropriate or minimum energy for melting and/or vaporizing the material without significantly melting undesirable portions of the material. For example, laser beams are a common form of a stream of energy that can be used to shape the endoprosthetic material. Additionally, there are instances where a laser is preferred over all other cutting techniques because of the nature of the resulting endoprosthesis as well as the characteristics of the endoprosthetic material.

For example, lasers typically used in cutting hardened steel, such as YAG or excimer lasers, can have a power of about 2,000 watts or greater. Some endoprosthetic materials can be shaped with lasers operating below about 2,000 watts, below about 1,000 watts, or below about 500 watts.

In one embodiment, an endoprosthesis may be manufactured as described herein using a femtosecond laser. A femtosecond laser may be desirable in producing an endoprosthesis in accordance with the multilayered composite structure of the present invention because it produces a smaller heat influence zone ("HIZ") compared to other lasers, or it can substantially eliminate the HIZ. In comparison, cutting an endoprosthesis using known methods can result in the tubular material being melted away, and thereby forming the pattern in the tubular member. Such melting can result in embrittlement of some materials due to oxygen uptake into the HIZ.

In one embodiment, electrical discharge machining is used to shape endoprosthetic material. As such, electrical discharge machining can is capable of cutting all types of conductive materials such as exotic metal including titanium, hastaloy, kovar, inconel, hard tool steels, carbides, and the like. In electrical discharge, the main interaction between the stream of-energy and the endoprosthetic material is thermal, where heat is generated by producing electrical discharges. This can lead to the endoprosthetic material being removed by melting and evaporation. Some examples of electrical discharge machining include wire electron discharge machining, CNC-controlled electrical discharge machining, sinker electrical discharge machining, small hole discharge machining, and the like.

In another embodiment, a charged particle beam can be used for shaping the endoprosthetic material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one embodiment, a stream of chemical matter can be used in order to shape or form holes in the endoprosthetic material. Chemical-jet milling, for example, provides selective and controlled material removal by jet and chemical action. As such, the process is similar to water-jet cutting, which is described in more detail below. In any event, chemical-jet milling can be useful for shaping various types of endoprosthetic materials, which provides intricate shaping capabilities.

In another embodiment, electrochemical shaping can be based on a controlled electrochemical dissolution process similar to chemical-jet milling an endoprosthetic material. As such, the endoprosthetic material can be attached to an electrical source in order to allow an electrical current to assist in the shaping.

In one embodiment, hydro-cutting or water-jet cutting can be used to shape an endoprosthetic material. Hydro-cutting is essentially a water-jet technology that uses the high force and high pressure of a stream of water directed at the endoprosthetic material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used. Hydro-cutting is particularly suitable for polymeric endoprosthesis, but can be used for metal materials when combined with abrasive particles, as described below.

A typical hydro-cutting apparatus for hardened materials can use about 2.5 gallons of water per minute directed at the endoprosthetic material at about 40,000 psi as a single stream. For example, a hydro-cutting apparatus in accordance with the present invention can use from about 0.25 gallon/minute to about 15 gallon/minute, from about 0.5 gallon/minute to about 10 gallons/minute, from about 1 gallon/minute to about 5 gallons/minute, or from about 2 gallons/minute to about 4 gallons/minute. However, it should be recognized that higher or lower flow rates can be used, and depend on the diameter and pressure of the flow.

Additionally, the hydro-cutting apparatus can jet the water at a force that ranges from about 50 psi to about 60,000 psi. This is because there are instances where lower pressures, such as from about 50 psi to 500 psi, can be used to ablate softer polymers, and some instances where more durable and harder materials may use from about 15,000 psi to about 60,000 psi, especially when shaping stronger and/or thicker materials. Additionally, water-jets similar to those used for washing purposes can jet the water at about 1,000 psi to about 5,000 psi in order to shape an endoprosthetic material of medium hardness. Thus, a wide range of water pressures can be employed.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention can be used with or without inclusion of such abrasives.

Additionally, one of the benefits of hydro-cutting is the ability to reutilize and recycle the spent water jet material. As such, the endoprosthetic material can be easily separated from the spent water, thereby enabling the recycling and reuse of the water during the hydro-cutting process.

In one embodiment, sandblasting, which fits into the regime of stream of matter cutting, can-be used to shape an endoprosthetic material by projecting a high energy stream of sand particles at the material. Sandblasting cuts materials in a manner similar to hydro-cutting, especially when the water-jet is doped with abrasive particulates. Additionally, various other particulate streams other than sand can be used in the stream-cutting techniques and machinery.

The presently described invention can relate to an endoprosthesis for delivery in a body lumen. The endoprosthesis can include at least a first strut element having a low stress zone, the low stress zone having a radiopaque composite material having a plurality of layers that includes at least one radiopaque layer. A first boundary region delineates adjacent layers and the first boundary region is configured to inhibit a crack from propagating between adjacent layers. The endoprosthesis can also include at least a second strut element having a high stress zone adjacent to the at least first strut element. The high stress zone can include a resiliently-flexible composite material having a plurality of layers that includes at least one resiliently-flexible layer. A second boundary region delineates adjacent layers, the second boundary region being configured to inhibit a crack from propagating between adjacent layers.

The first strut element of the endoprosthesis can be at least a portion of a crossbar and the second strut element can be at least a portion of an elbow coupled to the crossbar. The radiopaque composite material or resiliently-flexible composite material of the endoprosthesis can be a plurality of planar layers. Alternatively, radiopaque composite material or resiliently-flexible composite material of the endoprosthesis can be a plurality of concentric layers having at least one core.

The presently described invention can also relate another endoprosthesis for delivery in a body lumen. The endoprosthesis can include at least a first strut element having a low stress zone, the low stress zone being of a radiopaque composite material having a plurality of layers that includes at least one radiopaque layer. A first boundary region delineates adjacent layers, the first boundary region being configured to inhibit a crack from propagating between adjacent layers. The endoprosthesis can also include at least a second strut element having a high stress zone adjacent to the at least first strut element, the high stress zone being of a resiliently-flexible composite material having a plurality of layers that includes at least one resiliently-flexible layer. A second boundary region delineates adjacent layers, the second boundary region being configured to inhibit a crack from propagating between adjacent layers. Further, an additional layer-can extend along the first strut element and the second strut element.

The first strut element of the endoprosthesis can be at least a portion of a crossbar and the second strut element can be at least a portion of an elbow coupled to the crossbar. The radiopaque composite material or resiliently-flexible composite material of the endoprosthesis can be a plurality of planar layers. Alternatively, the radiopaque composite material or resiliently-flexible composite material includes a plurality of concentric layers having at least one core and one exterior layer, wherein at least one of the core or the exterior layer is the additional layer.

The radiopaque layers can include a material selected from the group consisting of palladium platinum, tungsten, silver, stainless steel, gold, tantalum, bismuth, barium sulfate, and combinations thereof. Further, the resiliently-flexible layer is comprised of a shape memory material, such as a shape memory alloy or a nickel titanium alloy.

The present invention can also relate to an endoprosthesis for delivery in a body lumen that includes a low stress zone and a high stress zone. The low stress zone can include a first plurality of layers, wherein a first boundary region delineates adjacent layers, the first boundary region being configured to inhibit a crack from propagating between adjacent layers. The high stress zone can be coupled to and continuous with the low stress zone. The high stress zone can include a second plurality of layers, wherein a second boundary region delineates adjacent layers, the second boundary region being configured to inhibit a crack from propagating between adjacent layers.

Optionally, the low stress zone and high stress zone are formed from a single substantially cylindrical tube having an outer layer continuous between the low stress zone and high stress zone, the high stress zone being resiliently flexible and having a bend configured to allow the endoprosthesis to close for delivery and open for deployment within a lumen.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A segmented substrate configured to receive one or more coatings and to be shaped into a crack-resistant endoprosthesis, the segmented substrate comprising:
   a first layered segment of said substrate including a first plurality of layers and having a first external surface and an opposite second external surface, the first external surface and the second external surface of the first layered segment defining a cross-sectional area having a first characteristic, the first layered segment being configured to be shaped into a first strut element having a low stress zone, said first plurality of layers of said first layered segment of said segmented substrate comprising:
      a first layer forming the first external surface;
      a second layer forming the second external surface, the second layer is not the first layer; and
      one or more first crack inhibiting boundary regions between said first layer and second layer, wherein said one or more first boundary regions are configured to inhibit a crack from propagating between said first layer and second layer, wherein at least said first layer and second layer cooperate in said first plurality of layers to provide said first characteristic to said low stress zone; and
   a second layered segment adjacent and connected to the first layered segment of said substrate including a second plurality of layers and having a third external surface and an opposite fourth external surface, the third external surface and the fourth external surface of the second layered segment defining a cross-sectional area having a second characteristic that is different than the first characteristic, the second layered segment being configured to be shaped into a second strut element having a bendable high stress zone, said second plurality of layers of said second layered segment of said segmented substrate comprising:
      a third layer forming the third external surface;
      a fourth layer forming the fourth external surface, the third layer is not the fourth layer; and
      one or more second crack inhibiting boundary regions between said third layer and said fourth layer, wherein said one or more second boundary regions are configured to inhibit a crack from propagating between said third layer and fourth layer, wherein at least said third layer and fourth layer cooperate in said second plurality of layers to provide said second characteristic to said high stress zone, the first plurality of layers being different from the second plurality of layers; and wherein said first layered segment and said second layered segment are configured to receive one or more coatings upon one or more of said first external surface, said second external surface, said third external surface and said fourth external surface.

2. A substrate as in claim 1, wherein said first layer and second layer of said first layered segment and/or said third layer and fourth layer of said second layered segment have a substantially planar orientation.

3. A substrate as in claim 1, wherein said one or more first and/or second boundary regions include a diffusion region that bonds said first layer to an adjacent layer of said first layered segment and/or bonds said third layer to an adjacent layer of said second layered segment.

4. A substrate as in claim 3, wherein said diffusion region includes a metallic interleaf layer.

5. A substrate as in claim 1, wherein said first layer and/or third layer is Nitinol and/or said second layer and/or fourth layer is a material selected from the group consisting of Ti3Al2.5V, Ti6Al4V, and Platinum.

6. A substrate as in claim 1, wherein said first layered segment and second layered segment each include a plurality of layers separated by a plurality of crack inhibiting boundary regions that inhibit crack propagation from one layer to an adjacent layer.

7. A substrate as in claim 1, wherein said first and second characteristics are selected from the group consisting of flexibility, rigidity, composition, layer composition, layer thickness, number of layers, shape memory, crack resistance, and combinations thereof.

8. A substrate as in claim 1, wherein said high stress zone is at an intersection of at least two strut elements and substantially devoid of being radiopaque.

9. A substrate as in claim 1, wherein said low stress zone is radiopaque.

10. A substrate as in claim 1, wherein said first layer, said second layer, said third layer, and said fourth layer are structurally significant.

11. A substrate as in claim 1, wherein the segmented substrate is a tube, sheet, or a rolled sheet before being shaped.

12. A segmented substrate configured to receive one or more coatings and to be shaped into a crack-resistant endoprosthesis, the segmented substrate comprising:
    a first layered segment of said segmented substrate including a first plurality of layers and having a first external surface and an opposite and different second external surface, the first external surface and the second external surface of the first layered segment defining a cross-sectional area having a first characteristic, the first layered portion being configured to be shaped into a first strut element having a low stress zone, said first plurality of layers of said first layered segment of said segmented substrate comprising:
        a first layer comprised of a first material forming the first external surface; and
        a second layer comprised of a second material bound to said first layer at a first crack inhibiting boundary region, wherein said first crack inhibiting boundary region is configured to inhibit a crack from propagating between said first layer and second layer, wherein at least said first material and second material cooperate in said first plurality of layers to provide said first characteristic to said low stress zone; and
    a second layered segment of said substrate including a second plurality of layers and having a third external surface and an opposite and different fourth external surface, the third external surface and the fourth external surface of the second layered segment defining a cross-sectional area having a second characteristic that is different from the first characteristic, the second layered segment being configured to be shaped into a second strut element having a bendable high stress zone, said second plurality of layers of said second layered segment of said segmented substrate comprising:
        a third layer comprised of a third material forming the third external surface; and
        a fourth layer comprised of a material different from the third material bound to said third layer at a second crack inhibiting boundary region, wherein said second crack inhibiting boundary region is configured to inhibit a crack from propagating between said third layer and said fourth layer, wherein at least said third layer and fourth layer cooperate in said second plurality of layers to provide said second characteristic to said high stress zone, the first plurality of layers being different from the second plurality of layers,
        wherein the segmented substrate is configured to be shaped into the crack-resistant endoprosthesis having at least one high stress section disposed between and coupling two low stress sections, said low stress sections including a first set of interconnected strut members defining at least a first annular element having a plurality of low stress zones, and said at least one high stress section including an interconnector that includes a bendable high stress zone, and
        wherein the low stress sections are fabricated from the first layered segment of the segmented substrate and the high stress sections are fabricated from the second layered segment of the segmented substrate; and
    wherein said first layered segment and said second layered segment are configured to receive one or more coatings upon one or more of said first external surface, said second external surface, said third external surface and said fourth external surface.

13. A substrate as in claim 12, wherein said first layer and second layer of said first layered segment and/or third layer and fourth layer of said second layered segment have a substantially planar orientation.

14. A substrate as in claim 12, wherein said first crack inhibiting boundary region is a diffusion region that bonds said first layer to said second layer and/or said second crack inhibiting boundary region is a diffusion region that bonds said third layer to said fourth layer.

15. A substrate as in claim 14, wherein said first material has a different composition from said second material and said third material, and said second material has a different composition from said third material.

16. A substrate in claim 14, wherein said diffusion region includes a metallic interleaf layer.

17. A substrate as in claim 12, wherein said first layered segment and second layered segment each include a plurality of layers bound together at a plurality of crack inhibiting boundary regions that inhibit crack propagation from one layer to an adjacent layer.

18. A substrate as in claim 12, wherein said first and second characteristics are selected from the group consisting of flexibility, rigidity, composition, layer composition, layer thickness, number of layers, shape memory, crack resistance, and combinations thereof.

19. A substrate as in claim 12, wherein said high stress zone is at an intersection of at least two strut elements and substantially devoid of being radiopaque, and low stress zone is radiopaque.

20. A substrate as in claim 12, the segmented substrate being configured to be shaped into:
   at least a second set of interconnected strut members defining at least a second annular element, the interconnected strut members of the second annular element including a plurality of low stress crossbar sections that are coupled by a plurality of high stress elbow sections and/or a plurality of high stress foot extension sections, each foot extension including a first foot portion, a second foot portion, and a toe portion; and
   the first annular element being coupled to the second annular element with at least one low stress interconnector element that connects at least one elbow section and/or at least one foot section from the first annular element to at least one elbow section and/or at least one foot section from the second annular element,
   the low stress sections being fabricated from the first layered segment of the segmented substrate and the high stress sections being fabricated from the second layered segment of the segmented substrate, wherein the at least one interconnector element is fabricated from the first layered segment of said segmented substrate.

21. A substrate as in claim 12, wherein the segmented substrate is a tube, sheet, or a rolled sheet before being shaped.

* * * * *